(12) United States Patent
Simó Canonge et al.

(10) Patent No.: US 11,013,738 B2
(45) Date of Patent: May 25, 2021

(54) DIPEPTIDYL PEPTIDASE-4 INHIBITORS FOR TOPICAL EYE TREATMENT OF RETINAL NEURODEGENERATIVE DISEASES

(71) Applicant: FUNDACIÓ HOSPITAL UNIVERSITARI VALL D'HEBRON-INSTITUT DE RECERCA, Barcelona (ES)

(72) Inventors: Rafael Simó Canonge, Sant Cugat del Vallès (ES); Cristina Hernández Pascual, Barcelona (ES)

(73) Assignee: FUNDACIÓ HOSPITAL UNIVERSITARI VALL D'HEBRON—INSTITUT DE RECERCA, Barcelona (ES)

( * ) Notice: Subject to any disclaimer, the term of this patent is extended or adjusted under 35 U.S.C. 154(b) by 0 days.

(21) Appl. No.: 16/095,621

(22) PCT Filed: Apr. 28, 2017

(86) PCT No.: PCT/EP2017/060234
§ 371 (c)(1),
(2) Date: Oct. 22, 2018

(87) PCT Pub. No.: WO2017/186934
PCT Pub. Date: Nov. 2, 2017

(65) Prior Publication Data
US 2019/0134030 A1 May 9, 2019

(30) Foreign Application Priority Data
Apr. 29, 2016 (EP) .................... 16382190

(51) Int. Cl.
| | | |
|---|---|---|
| A61K 31/4985 | (2006.01) |
| A61K 31/522 | (2006.01) |
| A61K 31/403 | (2006.01) |
| A61K 31/496 | (2006.01) |
| A61K 31/513 | (2006.01) |
| A61K 31/4162 | (2006.01) |
| A61K 38/26 | (2006.01) |
| A61K 9/00 | (2006.01) |
| A61K 9/06 | (2006.01) |
| A61K 9/08 | (2006.01) |
| A61P 27/06 | (2006.01) |
| A61K 31/40 | (2006.01) |
| A61K 31/00 | (2006.01) |
| A61K 31/155 | (2006.01) |
| A61K 31/519 | (2006.01) |
| A61K 45/06 | (2006.01) |
| A61K 47/02 | (2006.01) |

(52) U.S. Cl.
CPC ........ *A61K 31/4985* (2013.01); *A61K 9/0048* (2013.01); *A61K 9/06* (2013.01); *A61K 9/08* (2013.01); *A61K 31/00* (2013.01); *A61K 31/155* (2013.01); *A61K 31/40* (2013.01); *A61K 31/403* (2013.01); *A61K 31/4162* (2013.01); *A61K 31/496* (2013.01); *A61K 31/513* (2013.01); *A61K 31/519* (2013.01); *A61K 31/522* (2013.01); *A61K 38/26* (2013.01); *A61K 45/06* (2013.01); *A61K 47/02* (2013.01); *A61P 27/06* (2018.01)

(58) Field of Classification Search
CPC .... A61K 31/4985; A61K 9/0048; A61K 9/06; A61K 9/08; A61K 31/00; A61K 31/155; A61K 31/40; A61K 31/403; A61K 31/4162; A61K 31/496; A61K 31/513; A61K 31/519; A61K 31/522; A61K 38/26; A61K 45/06; A61K 47/02; A61P 27/06
See application file for complete search history.

(56) References Cited

U.S. PATENT DOCUMENTS

2008/0221200 A1  9/2008  Allison et al.

FOREIGN PATENT DOCUMENTS

EP  2444094 A1  4/2012

OTHER PUBLICATIONS

International Search Report and Written Opinion dated Aug. 16, 2017 for PCT Application No. PCT/EP2017/060234, 20 pages.
Abbott, Catherine, et al., "Cloning expression and chromosomal localization of a novel human dipeptidyl peptidase (DPP) IV homolog, DPP8", European Journal Biochem., Feb. 2000, vol. 267, pp. 6140-6150.
Aiello, Lloyd Paul "Targeting intraocular neovascularization and edema—one drop at a time", New England Journal of Medicine Aug. 28, 2008, vol. 359, No. 9, pp. 967-969.
Anderson, Peter JB, et al., "Glial and endothelial blood-retinal barrier resposes to amyloid-B in the neural retina of the rat", Clinical Ophthalmology 2008, vol. 2, No. 4, pp. 801-816.
Baetta, Roberta, et al., "Pharmacology of Dipeptidyl peptidase-4 inhibitors", Drugs 2011, vol. 71, No. 11, pp. 1441-1467.

(Continued)

*Primary Examiner* — Kortney L. Klinkel
*Assistant Examiner* — William Y Lee
(74) *Attorney, Agent, or Firm* — Squire Patton Boggs (US) LLP

(57) ABSTRACT

The invention relates to dipeptidyl peptidase-4 inhibitors, including saxagliptin and sitagliptin, for use in the topical eye treatment and/or prevention of retinal neurodegenerative diseases, in particular diabetic retinopathy and its associated microvascular impairment. The invention also encompasses pharmaceutical topical eye compositions for use in the topical treatment and/or prevention of these diseases.

12 Claims, 7 Drawing Sheets
Specification includes a Sequence Listing.

(56) References Cited

OTHER PUBLICATIONS

Bogdanov, Patricia, et al., "The db/bd Mouse: A useful model for the study of diabetic retinal neurodegeneration", PLOS One May 2014, vol. 9, Issue 5, e97302, pp. 1-18.

De Meester, Ingrid, et al., "CD26, let it cut or cut it down", Immunology Today, Aug. 1999, vol. 20, No. 8, pp. 367-375.

Dietrich, Nadine, et al., "The DPP4 inhibitor linagliptin protects from experimental diabetic retinopathy", PLOS One Dec. 12, 2016, e0167853, pp. 1-17.

Jung, Eunsoo, et al., "Gemigliptin, a dipeptidyl peptidase-4 inhibitor, inhibits retinal pericyte injury in db/bd mice and retinal neovascularization in mice with ischemic retinopathy", Biochimica et Biophysica Sep. 2015, vol. 1852, No. 12, pp. 2618-2629.

Kim Na-Hyung, et al., "The nonglycemic actions of dipeptidyl peptidase-4 inhibitors", Biomed Research International, Jul. 21, 2014, vol. 2014, Article ID 368703, 10 pages.

Lee, Choon-Soo, et al., "Dipeptidyl peptidase-4 inhibitor increases vascular leakage in retina through VE-cadherin phosphorylation", Scientific Reports Jul. 6, 2016, vol. 6, No. 1, pp. 1-16, DOI: 10.1038/srep29393.

Malhotra, Manjusha, et al., "Permeation through cornea", Indian Journal of Experimental Biology, Jan. 2001, vol. 39, pp. 11-24.

Marmor, Michael, et al., "Standard for clinical electroretinography (2004 Update)", Documenta Ophthalmologica 2004, vol. 108, pp. 107-114.

Nakamura, Yuya, et al., "Diabetes therapies in hemodialysis patients: dipeptidyl peptidase-4 inhibitors", World Journal of Diabetes Jun. 25, 2015, vol. 6, No. 6, pp. 840-849.

Pandit, Rahul S., et al., "Retinal and lens protective effet of sitagliptin in streptozotocin induced type-1 diabetic wistar rats", Biomedicine & Aging Pathology Jun. 2013, 3 pp. 65-73.

Prausnitz, Mark R., et al., "Permeability of cornea, sclera, and conjunctiva: a literature analysis for drug delivery to the eye", Journal of Pharmaceutical Sciences Dec. 1998, vol. 87, No. 12, pp. 1479-1488.

Schmidt, K.G., et al., "Neurodegenerative diseases of the retina and potential for protection and recovery", Current Neuropharmacology 2008, vol. 6, pp. 164-178.

Simo, Rafael, et al., "Neurodegeneration in the diabetic eye: new insights and therapeutic perspectives", Trends in Endocrinology and Metabolism, Jan. 2014, vol. 25, No. 1, pp. 23-33.

Simo, Rafael, et al., "Neurodegeneration is an early event in diabetic retinopathy: therapeutic implications", British Journal of Ophthalmology, Aug. 2012, vol. 96, pp. 1285-1290.

Simo, Rafael, et al., "Novel approaches for treating diabetic retinopathy based on recent pathogenic evidence", Progress in Retinal and Eye Research May 2015, vol. 48, No. 25, pp. 160-180.

Urtti, Arto "Challenges and obstacles of ocular pharmacokinetics and drug delivery", Advanced Drug Delivery Reviews Sep. 2006, vol. 58, No. 11, pp. 1131-1135.

Wronkowitz, Nina, et al., "Soluble DPP4 induces inflammation and proliferation of human smooth muscle cells via protease-activated receptor 2", Biochimia et Biophysica Acta, Jun. 11, 2014, vol. 1842, No. 9, pp. 1613-1621.

Zhang, Hui, et al., "Identification of novel dipeptidyl peptidase 9 substrates by two-dimensional differential in-gel electrophoresis", FEBS Journal Jul. 2015, vol. 282, pp. 3737-3757.

Abcouwer, et al., "Diabetic retinopathy: loss of neuroretinal adaptation to the diabetic metabolic environment", Ann NY Acad Sci. Apr. 2014, vol. 1311, pp. 174-190.

Antonetti, et al., "Mechanisms of Disease, Diabetic Retinopathy", The New England Journal Of Medicine, Mar. 29, 2012, vol. 366, No. 13, pp. 1227-1239.

Boddu, et al., "Drug delivery to the back of the eye following topical administration: an update on research and patenting activity", Recent Patents on Drug Delivery & Formulations 2014, vol. 8, pp. 27-36.

Carrasco, et al., "Lower somatostatin expression is an early event in diabetic retinopathy and is associated with retinal neurodegeneration", Pathology/Complications, Original Article Nov. 2007, vol. 30, No. 11, pp. 2902-2908.

Garcia-Ramirez, et al., "Interphotoreceptor retinoid-binding protein (IRBP) is downregulated at early stages of diabetic retinopathy", Diabetologia 2009, vol. 52, pp. 2633-2641.

Heintz, et al., "Prevalence and healthcare costs of diabetic retinopathy: a population-based register study in Sweden", Diabetologia 2010, vol. 53, pp. 2147-2154.

Hernandez, et al., "Topical administration of DPP-IV inhibitors prevents retinal neurodegeneration in experimental diabetes", Diabetologia 2017, Clinical, Translational and Experimental Diabetes and Metabolism, vol. 60, No. 11, pp. 2285-2298.

Thrimawithana, et al., "Drug delivery to the posterior segment of the eye", Drug Discovery Today Mar. 2011, vol. 16, Nos. 5/6, pp. 270-277.

Urtti, Arto, "Challenges and obstacles of ocular pharmacokinetics and drug delivery", Science Direct Advanced Drug Delivery Reviews, Sep. 2006, vol. 58, pp. 1131-1135.

Yau et al., "Global prevalence and major risk factors of diabetic retinopathy", Epidemiology/Health Research Original Article, Diabetes Care, Mar. 2012, vol. 35, pp. 556-564.

(A)

(B)

(A)

(B)

DIPEPTIDYL PEPTIDASE-4 INHIBITORS FOR TOPICAL EYE TREATMENT OF RETINAL NEURODEGENERATIVE DISEASES

This application claims the benefit of European Patent Application EP16382190.3 filed on Apr. 29, 2016.

The present invention relates to the field of medical approaches for ocular diseases that may lead to partial or total blindness. The invention provides the useful of a family of peptides—Dipeptidyl peptidase-4 (DPP-4) inhibitors—to be applied topically into the eyes.

BACKGROUND ART

Retinal neurodegenerative diseases refer to retinal conditions characterized by progressive neuronal loss. Diabetic retinopathy, age-related macular degeneration, glaucoma and retinitis pigmentosa are considered retinal diseases in which neurodegeneration plays an essential role.

An in depth analysis of these diseases, their critical sites, as well as of possible ways of protection and ways leading to recovery can be extracted from Schmidt et al., "Neurodegenerative Diseases of the Retina and Potential for the Protection and Recovery", *Current Neuropharmacology*—2008, Vol. No. 6, pp.: 164-178.

Diabetic retinopathy (DR) is the most common complication of diabetes and remains the leading cause of blindness among working-age individuals in developed countries. Current treatments for DR such as laser photocoagulation, intravitreous injections of corticosteroids or anti-VEGF agents are indicated in too advanced stages of the disease and are associated with significant adverse effects.

DR has been classically considered to be a microcirculatory disease of the retina. However, there are some data which suggest that retinal neurodegeneration is an early event in the pathogenesis of DR which participates in the microcirculatory abnormalities that occur in DR as can be deduced from Simó et al. on behalf of the European Consortium for Early Treatment of Diabetic Retinopathy (EUROCONDOR). "Neurodegeneration is an early event in diabetic retinopathy: therapeutic implications", *Br. J. Ophthalmol.*—2012, vol. 96, pp. 1285-1290. Other references mentioning approaches for treating DR are disclosed in Simó R, Hernández C, "Novel approaches for treating diabetic retinopathy based on recent pathogenic evidence", *Prog Retin Eye Res*—2015, vol. no. 48, pp.: 160-80; and Simó R, Hernández C; European Consortium for the Early Treatment of Diabetic Retinopathy (EUROCONDOR). "Neurodegeneration in the diabetic eye: new insights and therapeutic perspectives", *Trends Endocrinol Metab*—2014; vol. no. 25(1), pp.: 23-33.

In the case of DR the neurodegeneration (loss of effective neurons) occurs at the early stages of the disease and produces functional abnormalities such as the loss of both chromatic discrimination and contrast sensitivity. These alterations can be detected by means of electrophysiological studies in diabetic patients even with less than two years of diabetes duration, that is, before microvascular lesions can be detected under ophthalmologic examination. In addition, a delayed multifocal ERG (electroretinography) implicit time (mfERG-IT) predicts the development of early microvascular abnormalities. Furthermore, neuroretinal degeneration initiates and/or activates several metabolic and signaling pathways which will participate in the microangiopathic process, as well as in the disruption of the blood-retinal barrier (a crucial element in the pathogenesis of DR).

Blood retinal barrier (BRB) disruption (or breakdown) can be assessed by Optical Coherence Tomography (OCT).

The early stages of retinal neurodegenerative diseases or neurodegeneration associated with these pathologies are not currently treated, although they would prevent advanced lesions, such as microcirculatory problems leading to retinal edema and retinal neovascularization. Thus at early stages, in particular of DR, no treatment is applied and the standard follow-up of the patients is conducted.

On the other hand, when the early stages of these retinal neurodegenerative disease, in particular DR, are the therapeutic target, it would be inconceivable to recommend an aggressive treatment such as laser photocoagulation or intravitreous injections. To date, the use of eye drops has not been considered a good route for the administration of drugs addressed to preventing or arresting DR. This is because it is generally assumed that they do not reach the posterior segment of the eye (ie. the vitreous and the retina), as declared in Urtti A et al., "Challenges and obstacles of ocular pharmacokinetics and drug delivery". *Adv. Drug. Deliv. Rev.* 2006, vol. 58, pp. 1131-1135. Although there exists a little evidence that compounds administered in the cornea can reach the retina, they represent isolated cases and correspond to compounds of low molecular weight, such as those referred to in Aiello et al., "Targeting Intraocular Neovascularization and Edema—One Drop at a Time", *N. Eng. J Med*—2008, vol. 359, pp. 967-969. Aiello et al. show that in two different assays, a pyrrolidin derived compound (named TG100572, 4-chloro-3-(5-methyl-3-{[4-(2-pyrrolidin-I-ylethoxy)phenyl]amino}-1,2,4-benzotriazin-7-yl)phenol)) with the capability of acting as an inhibitor of kinases involved in neovascular generation and retinal edema, was able to reach the target in the retina once administered in the form of eye drops.

However, reaching the retina by passing through the cornea or the sclera is difficult and non-predictable, mainly due to the anatomic nature of this tissue. Topical drug application is useful in the treatment of many anterior segment disorders, but it is considered inefficient in delivering therapeutic concentrations of the drug to the posterior segment of the eye, owing to the unique anatomical, physiological and biochemical barriers of the eye.

There are two major pathways for moving fluids and solutes through cell layers: the transcellular pathway (active ionic transport with energy cost) and the paracellular pathway (mostly based on passive diffusion by gradient concentrations and permeation). Cornea is divided into 3 main complex layers: epithelium, stroma and endothelium. The corneal epithelium is lipophilic and consists of stratified squamous cells five to seven cell layers thick. Immediately posterior to the corneal epithelium, there is the collagenous Bowman's membrane. Posterior to Bowman's membrane it is found the hydrophilic, lamellar stroma. Since it's hydrophilic, the stroma is a strong barrier to lipophilic molecules, though it lacks tight-junction complexes. Next to the stroma lies the single-cell layer of Descemet's membrane and the extracellular matrix secreted by the deepest layer of the cornea, the endothelium. The corneal endothelium is a single cuboidal cell layer in thickness, and is a lipophilic region responsible for permitting leakage of nutrients from the aqueous humour to the cornea and for transporting water from the avascular cornea into the anterior chamber. Thus, the lipophilic-hydrophilic-lipophilic nature of the cornea, as illustrated, is a major contributor to the challenge of any drug permeability.

Besides, also the lipophilic and hydrophilic nature of the drugs, sometimes both present in a single drug, put additional challenges. So that, a drug can easily permeate through one of the layers but it is impeded through the others. At this respect, it is not only the molecular weight of a compound the limiting rate, but also other features, such as hydrophobicity, lipophilicity, solubility in each of the structures are limiting factors (See Malhotra et al., "Permeation through cornea", *Indian Journal of Experimental Biology*—2001, vol. no. 39, pp.: 11-24). All these parameters make really difficult that a compound, even having low molecular weights (<180 Da), could reach internal eye parts (vitreous humour or retina) through the cornea. Therefore, even if one drug can pass through, this does not mean that another drug with the same molecular weight can reach inner parts of eye.

In the same way, permeability of sclera and conjunctiva to drugs in order to reach retina is highly complicate and strongly dependent on many of the nature features of a drug. Particularly referring to these difficulties it is mentioned the extensive work of Prausnitz et al., "Permeability of Cornea, Sclera, and Conjunctiva: A Literature Analysis for Drug Delivery to the Eye", *Journal of Pharmaceutical Sciences*—1998, vol. no. 87(12), pp.: 1479-1488.

For all these reasons there is not nowadays any marketed composition for ophthalmic (topically into eye) treating any diseases of the retina.

DPP-4 inhibitors are a relatively new class of oral diabetes drugs, also known as gliptins, which are prescribed for people with type 2 diabetes. They work by blocking the action of DPP-4, an enzyme which destroys a group of gastrointestinal hormones called incretins (mainly glucagon-like peptide-1, GLP-1). Incretins help stimulate the production of insulin when it is needed (e.g. after eating) and reduce the production of glucagon by the liver when it is not needed (e.g. during digestion).

Dipeptidyl peptidase-4 (DPP-4, or DPP-IV), also known as adenosine deaminase complexing protein 2 or CD26 (cluster of differentiation 26) is a protein that, in humans, is encoded by the DPP4 gene. It is a highly conserved peptidase with high selectivity for peptides with a proline or alanine at the second NH2-terminal position. The gene encodes a type II transmembrane protein of 766 amino acids, which is anchored to the lipid bilayer by a single hydrophobic segment located at the N-terminus and has a short cytoplasmic tail of six amino acids (see De Meester I et al., "CD26, let it cut or cut it down", *Immunol Today*—1999, vol. no. 20, pp.: 367-375). The extracellular part of CD26 contains a glycosylation domain, a cysteine-rich domain, and a catalytic domain. DPP-4 preferentially cleaves N-terminal dipeptides from proteins and oligopeptides containing proline or alanine in the penultimate position (Xaa-Pro- or Xaa-Ala-) (see Abbott, et al., "Cloning, expression and chromosomal localization of a novel human dipeptidyl peptidase (DPP) IV homolog, DPP8", *Eur J Biochem*—2000; vol. no. 267, pp.: 6140-50). Substrates of DPP-4 include numerous neuropeptides (i.e. Substance P), hormones (i.e. GLP-1, GLP-2, insulin growth factor-1, neuropeptide-Y, peptide YY, growth hormone-releasing hormone, erythropoietin) and chemokines (i.e. IP-10, RANTES, stromal cell-derived factor-1)(see Kim et al., "The Nonglycemic Actions of Dipeptidyl Peptidase-4 Inhibitors"—*BioMed Research International* Volume 2014, Article ID 368703).

Despite a common mechanism of action, there is a significant heterogeneity in the pharmacokinetic of different DPP-4 inhibitors (DI). So, they show differences in half-life, bioavailability, metabolism, and excretion route. Some DPP-4 inhibitors act through competitive enzymatic inhibition (sitagliptin and alogliptin) while others are substrate-enzyme blockers (saxagliptin and vildagliptin) (see Baetta et al., "Pharmacology of dipeptidyl peptidase-4 inhibitors: similarities and differences", *Drugs*—2011, vol. no. 71, pp.: 1441-1467).

Diabetes is a group of chronic diseases characterized by hyperglycemia. To prevent diabetic complications it is essential to reduce hyperglycemia using blood glucose lowering agents. The administration of any antidiabetic drug, such as DPP-4 inhibitors, can improve or attenuate DR symptoms, since the leading cause or the origin of the disease, in particular the high levels of glucose in blood, is at final instance improved.

At this respect, one document showing the active role of gemigliptin (DPP-4 inhibitor) on diabetic retinopathy is the one of Jung et al., "Gemigliptin, a dipeptidyl peptidase-4 inhibitor, inhibits retinal pericyte injury in db/db mice and retinal neovascularization in mice", *Biochimica et Biophysica Acta, Molecular Basis of Disease*—2015, vol. no. 1852(12), pp.: 2618-2629. Jung et al. disclose that gemigliptin orally administered in diabetic mice (db/db) can ameliorate retinal pericyte apoptosis and vascular leakage in these mice.

However, nowadays there are no data regarding a direct beneficial effect on the retina of these inhibitors. In this regard, it should further be noted that DPP-4 inhibitors do not pass the blood-brain barrier. Given that blood-brain barrier and BRB are quite similar it is also broadly assumed and more than probably that they do not pass BRB. In the remote case that some quantity of DPP-4 inhibitors could pass BRB, high doses will be required to reach the retina at therapeutic concentrations thus increasing the possibility of systemic adverse effects.

In PCT application WO2014131815 it was surprisingly found that, despite their high molecular weight retinal, topical eye administration of some GLP-1 agonists, as well as GLP-1 itself, could prevent neurodegenerative process occurring in the early stages of diabetic retinopathy. In this document, inventors also provided evidence that other retinal diseases in which neurodegeneration plays an essential role may be treated and/or prevented with the topical ocular administration (eye drops) of these compounds.

At present, alternative treatments for retinal neurodegenerative diseases are needed. In the particular case of DR and its associated retinal microvascular impairment or damage, alternative treatments for the background retinopathy or non-proliferative DR, as well as for protecting the neuroretina from damage (leading to loss of neurons). Therefore, new pharmacological treatments for the early stages of the disease, when neurodegeneration seems to be starting are needed. Early treatment of DR, and of any other retinal neurodegeneration, will be effective in reducing the progression to advanced stages needing aggressive therapies such as laser photocoagulation, intravitreal injections of corticosteroids or anti-VEGF agents, or surgical intervention.

SUMMARY OF THE INVENTION

The inventors have found that DDP-4 is present in human retina and highly expressed in the retina, namely in retinal pigment epithelium (RPE) of patients suffering from diabetes. Inhibitors of DPP-4 enzyme (acting through competitive enzymatic inhibition, such as sitagliptin, or being substrate-enzyme blockers, such as saxagliptin) have been tested and surprisingly they reached the retina when applied topically in the eye (i.e. in the cornea or conjunctival fornix or sclera, that is ophthalmic application to surface of the eye), despite their molecular weights and complexity of structures. These inhibitors were even able to protect and prevent the retina from degeneration and vascular leakage. These compounds acted as neuroprotectors of the retina (in particular the neuroretina, which is the part of the retina including the neurons but without the retinal pigment epithelium).

It should be emphasized that the topical administration of the inhibitors according to the invention, not only reach the retina, but also achieve effective concentrations for abrogating the evolution of early stages of DR by preventing BRB disruption and by preventing or treating microvascular impairment associated with DR. This impairment is mainly detected by protein retinal vascular leakage.

Thus, in a first aspect the invention relates to DPP-4 inhibitors or a pharmaceutically acceptable salt or solvate thereof, for use in the topical eye treatment and/or prevention of a retinal neurodegenerative disease.

The topical eye treatment and/or prevention is a treatment and/or prevention, thus applied onto the eye surface (i.e. in the cornea, sclera or conjunctival fornix), due to the fact that surprisingly and unexpectedly these inhibitors can reach the retina when applied topically to eyes (that is ophthalmic drug administration). This applies to any of the embodiments and combination of embodiments disclosed in the present invention.

Considering the state of the art, it was unexpected that molecules of a high molecular weights and chemically complex in terms they have hydrophobic (lipophilic) and hydrophilic parts, would be able to reach the retina once administered topically in the corneal surface, sclera or conjunctiva. As above exposed, for a compound to be applied in the cornea, sclera or conjunctival fornix and then to be able to reach the retina, several barriers with different lipophilic and hydrophilic nature have to be overcome. Thus, the invention supposes a real contribution to the art for demonstrating that the DPP-IV inhibitors, commonly used anti-diabetic drugs, can also be applied topically onto the eye, in order to promote prevention of some of the more disabling accompanying diseases in diabetes; the retinal neurodegenerative diseases including in particular diabetic retinopathy.

Thus, also a long-felt need in the field of ophthalmology has been solved by providing DPP-4 inhibitors that, by means of topical eye administration or as ingredients of topical compositions (thus topical eye compositions) can reach the retina and exert therein a neuroprotection effect. In addition, the topical administration of these inhibitors limits their action to the eye and minimises the associated systemic adverse effects.

This aspect of the invention can also be formulated as the use of dipeptidyl peptidase-4 inhibitors or a pharmaceutically acceptable salt or solvate thereof, for the manufacture of a medicament for the topical eye treatment and/or prevention of retinal neurodegenerative diseases, in particular for the topical eye treatment and/or prevention of the retinal damage in early stages of retinal neurodegenerative diseases and its associated retinal microvascular impairment or damage, in particular early stages of DR, due to the neuroprotective effect of the inhibitors. The present invention also relates to a method for the topical eye treatment and/or prevention of retinal neurodegenerative diseases, in particular for neuroprotection in early stages of retinal neurodegenerative diseases, in particular early stages of DR and its associated retinal microvascular impairment or damage, comprising administering (meaning topically administering in the eye) a dipeptidyl peptidase-4 inhibitor or a pharmaceutically acceptable salt or solvate thereof, together with topical pharmaceutically or veterinary acceptable excipients and/or carriers, in a subject in need thereof, including a human.

Further, inventors demonstrate that by inhibiting retinal DPP-4, thus directly acting through this enzyme sited in the retina, retinal neurodegenerative diseases, in particular with early stages of retinal neurodegenerative diseases and its associated retinal microvascular impairment or damage, can be treated not as a secondary effect of lowering blood glucose levels, but due to a direct action on the retinal enzyme. Therefore, the invention also relates to DPP-4 inhibitors or a pharmaceutical or veterinary acceptable salt thereof, for use in the treatment and/or prevention of a retinal neurodegenerative disease; in particular for the topical eye treatment and/or prevention of the retinal damage in early stages of retinal neurodegenerative diseases and its associated retinal microvascular impairment or damage.

Another aspect of the invention is a pharmaceutically or veterinary topical eye composition for use in the topical eye treatment and/or prevention of a retinal neurodegenerative disease, which comprises an effective amount of a dipeptidyl peptidase-4 inhibitor, or a pharmaceutically or veterinary acceptable salt or solvate thereof, and mixtures thereof, together with topical pharmaceutically or veterinary acceptable excipients and/or carriers.

Yet a final aspect are pharmaceutical or veterinary topical compositions comprising a therapeutically effective amount of a DPP-4 inhibitor, or a pharmaceutically or veterinary acceptable salt thereof, together with topical pharmaceutically or veterinary acceptable excipients and/or carriers, wherein the composition has a dynamic viscosity from $5.0 \times 10^{-4}$ Pa·s to 300 Pa·s, at 20° C., a pH from 4.5 to 9.0 and wherein the dipeptidyl peptidase-4 inhibitor is in a concentration from 5 mg/ml to 200 mg/ml in relation to the final volume of the composition.

DETAILED DESCRIPTION OF THE INVENTION

Figure 1:
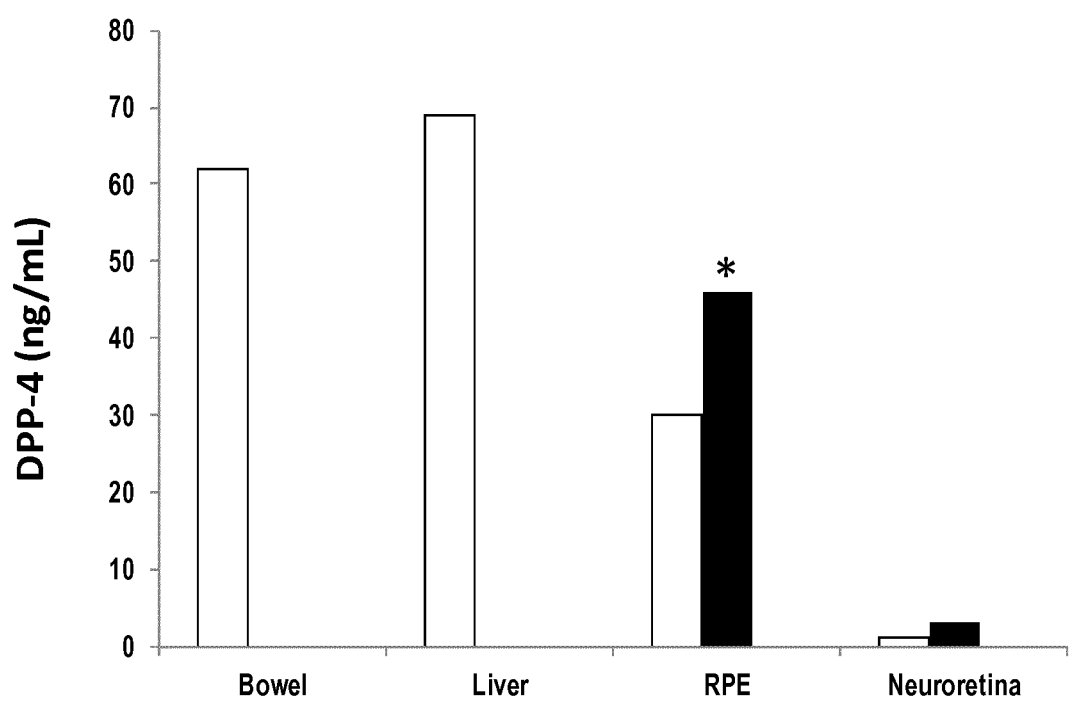
FIG. 1 is a graphic with bars showing DPP-4 concentration (ng/ml) in bowel, liver and human retina (RPE and neuroretina). White bars: non-diabetic donors. Black bars: diabetic donors. *$p<0.05$

For the sake of understanding, the following definitions are included.

In the sense of the invention, the term "neuroprotection" means any kind of treatment or prophylactic method that can be used in order that neurons constituting the neuroretina remain preserved and in a physiological state corresponding to the one of a health subject animal (including humans). The "neuroretina" is the part of the retina including the neurons and without the retinal pigment epithelium. Neuroretina is the responsible of the visual cycle.

The expression "neuroprotection in the early stages of diabetic retinopathy" relates to any treatment or prophylactic method carried out before advanced stages of DR are established.

For "early stages of diabetic retinopathy" is to be understood as the time in which, due to the presence of diabetes, functional abnormalities can be detected in the eye (i.e. chromatic discrimination, contrast sensitivity and electroretinography abnormalities), but the pattern of microvascular changes of DR has not yet been fully established, that is, there cannot be observed the typical lesions of non-proliferative DR.

For "retinal microvascular impairment or damage associated to diabetic retinopathy" is to be understood as encompassing those retinal microvascular abnormalities, such as generalized and focal arteriolar narrowing, and arteriovenous nicking that reflect cumulative vascular damage due to diabetic retinopathy (in early or late stages of the disease. This retinal microvascular impairment or damage is mainly detected by the presence of retinal vascular leakage allowing the detection of proteins (such as albumin extravasation) from blood inside the retinal blood vessels to the different retinal layers.

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The term "pharmaceutically or veterinary acceptable" as used herein pertains to compounds, materials, compositions, and/or dosage forms which are, within the scope of sound medical and veterinary judgment, suitable for use in contact with the tissues of a subject (e.g. human or any other animal) without significant toxicity, irritation, allergic response, or other problem or complication, commensurate with a reasonable benefit/risk ratio. Each carrier, excipient, etc., must also be "acceptable" in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. Suitable carriers, excipients, etc. can be found in standard pharmaceutical texts, and include, as a way of example preservatives, agglutinants, humectants, emollients, and antioxidants.

As above exposed, the inventors propose a new therapeutically approach for retinal neurodegenerative diseases (retinal diseases in which neurodegeneration plays an essential role) that, besides being non-aggressive, is useful in the treatment of the early stages of these diseases, and, in particular in the treatment of the early stages of DR and associated DR retinal microvascular impairments, detected by retinal vascular leakages.

In a particular embodiment of the first aspect of the invention, DPP-4 inhibitor is for use by inhibition of retinal dipeptidyl peptidase-4. That is, the topical treatment into the eye takes place due to direct inhibition of DPP-4 enzyme in the retina.

In another particular embodiment, DPP-4 inhibitors are selected from the group consisting of sitagliptin, saxagliptin, vildagliptin, linagliptin, anagliptin, teneligliptin, alogliptin, trelagliptin, gemigliptin, omarigliptin, their pharmaceutically acceptable salts or solvates, and mixtures thereof.

In a particular embodiment of the first aspect of the invention, the DPP-4 inhibitor for use as above exposed, is a DPP-4 competitive enzymatic inhibitor and it is selected from the group consisting of sitagliptin, linagliptin, alogliptin, their pharmaceutically acceptable salts or solvates, and mixtures thereof.

In yet another particular embodiment of the first aspect of the invention, DPP-4 inhibitors for the topical eye treatment and/or prevention of retinal neurodegenerative diseases is a DPP-4 substrate-enzyme blocker, and it is selected from the group consisting of a compound of formula saxagliptin, vildagliptin, anagliptin, their pharmaceutically acceptable salts or solvates, and mixtures thereof.

In yet a more particular embodiment the DPP-4 inhibitor is saxagliptin. In another also more particular embodiment, the DPP-4 inhibitor is sitagliptin.

Chemical formulas of all these particular compounds are listed herewith. According to its structural formula, DPP-4 inhibitors can be grouped by similar functional groups or by similar parts of the molecules:

| Formula DPP-4 inhibitor | Name; IUPAC name |
|---|---|
| 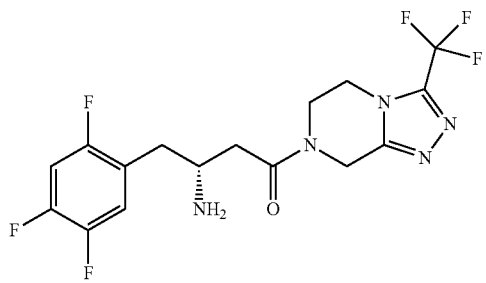 [SMILES: N[C@@H](CC(=O)N1CCn2c(nnc2C(F)(F)F)C1)Cc1cc(F)c(F)cc1F] | Sitagliptin; (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine |
| 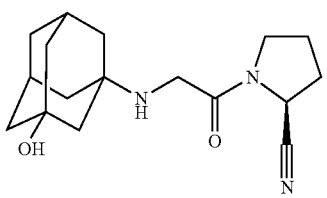 [SMILES: N#C[C@@H]1CCCN1C(=O)CNC12CC3CC(CC(O)(C3)C1)C2] | Vildagliptin; (S)-1-[N-(3-hydroxy-1-adamantyl)glycyl]pyrrolidine-2-carbonitrile |
| 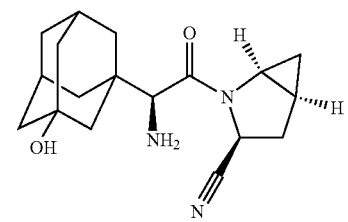 [SMILES: N#C[C@@H]1C[C@@H]2C[C@@H]2N1C(=O)[C@@H](N)C12CC3CC(CC(O)(C3)C1)C2] | Saxagliptin; (1S,3S,5S)-2-[(2S)-2-amino-2-(3-hydroxy-1-adamantyl)acetyl]-2-azabicyclo[3.1.0]hexane-3-carbonitrile |
| 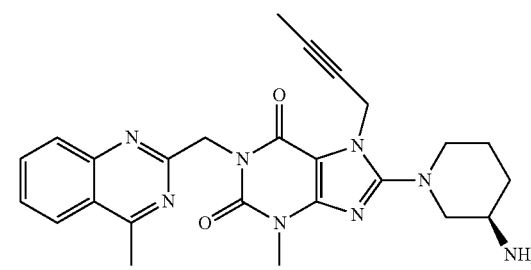 | Linagliptin; 8-[(3R)-3-aminopiperidin-1-yl]-7-(but-2-yn-1-yl)-3-methyl-1-[(4-methylquinazolin-2-yl)methyl]-3,7-dihydro-1H-purine-2,6-dione |
| 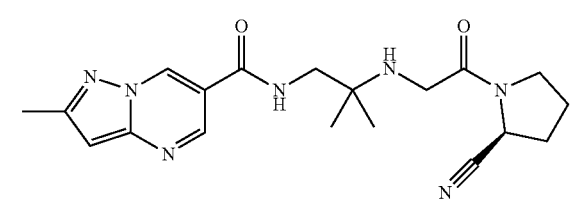 [SMILES: Cc1cc2ncc(C(=O)NCC(C)(C)NCC(=O)N3CCC[C@H]3C#N)cn2n1] | Anagliptin; N-[2-[[2-[(2S)-2-Cyanopyrrolidin-1-yl]-2-oxoethyl]amino]-2-methylpropyl]-2-methylpyrazolo[1,5-a]pyrimidine-6-carboxamide |
| 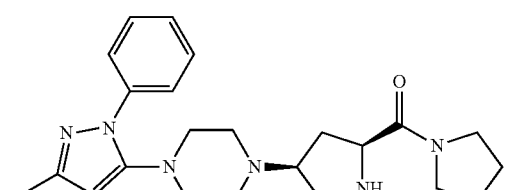 | Teneligliptin; {(2S,4S)-4-[4-(3-Methyl-1-phenyl-1H-pyrazol-5-yl)-1-piperazinyl]-2-pyrrolidinyl}(1,3-thiazolidin-3-yl)methanone |

| Formula DPP-4 inhibitor | Name; IUPAC name |
|---|---|
| 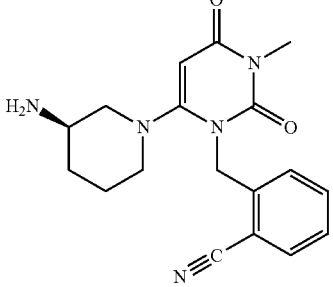 | Alogliptin; 2-({6-[(3R)-3-aminopiperidin-1-yl]-3-methyl-2,4-dioxo-3,4-dihydropyrimidin-1(2H)-yl}methyl)benzonitrile |
| 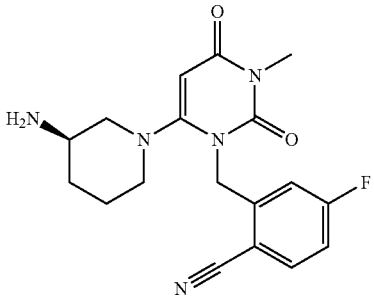 | Trelagliptin; Succinic acid-2-({6-[(3R)-3-amino-1-piperidinyl]-3-methyl-2,4-dioxo-3,4-dihydro-1(2H)-pyrimidinyl}methyl)-4-fluorobenzonitrile (1:1) |
| 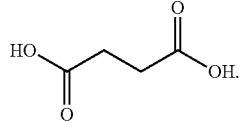 | Gemigliptin; (3S)-3-amino-4-(5,5-difluoro-2-oxopiperidino)-1-[2,4-di(trifluoromethyl)-5,6,7,8-tetrahydropyrido[3,4-d]pyrimidin-7-yl]butan-1-one |
| 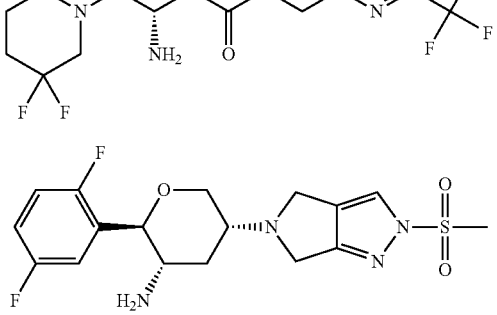 | Omarigliptin; (2R,3S,5R)-2-(2,5-difluorophenyl)-5-(2-methylsulfonyl-4,6-dihydropyrrolo[3,4-c]pyrazol-5-yl)oxan-3-amine |

Other usable DPP-4 inhibitors are dutogliptin (and its tartrate salt), and lupeol.

In a particular embodiment, the DPP-4 inhibitor for use in the topical eye treatment and/or prevention according to the invention, is for use in the treatment and/or prevention of retinal neurodegenerative disease selected from the group consisting of DR, age-related macular degeneration, glaucoma and retinitis pigmentosa.

In a preferred embodiment, the DPP-4 inhibitor is for use in the treatment and/or prevention of diabetic retinopathy and associated to DR retinal microvascular impairment. This means that retinal microvascular impairment or damage taking place in DR, and usually detected by retinal vascular leakage of proteins in the retinal layers, can be treated with the topical eye administration of the DPP-4 inhibitors.

Further, in another preferred embodiment, the DPP-4 inhibitor is for use in the topical eye treatment and/or prevention of the early stages of DR.

In particular, at these early stages when DR is not established yet, the inhibitors of the invention applied topically act as neuroprotector agents of the neuroretina, thus exerting a neuroprotection effect as will be illustrated in the examples below. Neurons are preserved from damage and loss of function, and they are maintained in a health physiological state. The same reasoning applies with the other retinal neurodegenerative diseases. Indeed, the peptides can be used due to its neuroprotective properties.

A brief summary of the diabetic retinopathy development is next exposed. The metabolic pathways triggered by hyperglycemia, and hyperglycemia itself, lead to DR but a period of at least five years is required before DR can be diagnosed under ophthalmoscopic examination. The first stage that can be seen is background retinopathy or non-proliferative diabetic retinopathy (NPDR) (which is constituted by microaneurysms, microhemorrhages and hard exudates). At this stage there is no specific treatment but the standard follow-on of the diabetic subject. From this stage the natural history of the disease can follow two directions that do not exclude the other. One of them is the development of clinically significant diabetic macular edema (DMO) in which the most important pathogenic element is the breakdown of the blood retinal barrier (BRB). This way is more frequent in type 2 diabetic patients. The other direction is towards proliferative diabetic retinopathy (PDR), which is more frequent in type 1 diabetes. In this later setting capillary occlusion plays an essential role generating an imbalance between angiogenic and antiangiogenic factors, which finally stimulates neovascularization (the hallmark of PDR). However, even before NPDR could be detected in the ophthalmologic examination, retinal neurodegeneration and vascular leakage does exist. Aggressive treatments are performed when DMO and PDR is established. These treatments include photocoagulation (PGC), intravitreous injections of corticosteroids and/or anti vascular endothelial growth factor agents (IVTR), and vitrectomy (VTR).

With the DDP-4 inhibitors for use in the topical eye treatment and/or prevention of DR according to the invention, some of these aggressive treatments can be avoided if in the early stages of the disease, when functional abnormalities (i.e. chromatic discrimination, contrast sensitivity and electroretinography abnormalities) and vascular leakage can be detected, the subject receives compounds aiding the neuroprotection of the retina. So that, if the retina is protected from the consequences of chronic blood glucose levels, major complications can be minimized, or even never appear with the real improvement of life quality of diabetic patients. The topical administration to eye of the DPP-4 inhibitors disclosed above represents a real advantage, avoiding further aggressive treatments.

The protection of retinal neurodegeneration detected by means of several ophthalmological examinations represents a good approach for treating DR before vascular abnormalities are developed. In the early stages of DR neurodegeneration exists (which can be detected by the loss of both, chromatic discrimination and contrast sensitivity, glial activation and apoptosis of neural cells). The DPP-4 inhibitors for topical administration (topical administration to the eye) of the invention are useful in these early stages when no treatment is indicated and only the follow-up is recommended until more advances stages of DR are established (clinically significant diabetic macular edema and/or proliferative diabetic retinopathy).

Treatment in the early stages of DR has the real advantage that further complications are avoided, namely microaneurysms, microhemorrhages, hard exudates, capillary occlusion, and neovascularization.

In another embodiment, the DPP-4 inhibitors for use according to the invention, are ingredients (components) of pharmaceutically or veterinary topical eye compositions, said compositions comprising at least one DPP-4 inhibitor as defined above and any pharmaceutically or veterinary topical acceptable carriers and/or excipients.

As above exposed another object of the invention is a pharmaceutically or veterinary topical composition for use in the topical eye treatment and/or prevention of a retinal neurodegenerative disease, which comprises an effective amount of a dipeptidyl peptidase-4 inhibitor, or a pharmaceutically or veterinary acceptable salt or solvate thereof, and mixtures thereof, together with topical pharmaceutically or veterinary acceptable excipients and/or carriers.

In a particular embodiment of this second aspect of the invention, the pharmaceutically or veterinary topical eye compositions for use in the topical eye treatment and/or prevention of retinal neurodegenerative diseases, it comprises at least one DPP-4 inhibitor selected from the group consisting of sitagliptin, saxagliptin, vildagliptin, linagliptin, anagliptin, teneligliptin, alogliptin, trelagliptin, gemigliptin, omarigliptin. Particular carriers and/or excipients relate to water, saline buffers, and mixtures of water in oil or oil in water. Particular excipients are selected from preservatives, agglutinants, humectants, emollients, and antioxidants.

In a particular embodiment of this second aspect of the invention, the pharmaceutically or veterinary topical eye compositions for use as above indicated, further comprises a compound selected from the group consisting of mammal GLP-1, particularly human GLP-1 (UniProt: P01275), liraglutide, exenatide, lixisenatide, its salts and mixtures thereof.

GLP-1 (glucagon-like peptide-1) is an endogenous insulinotropic peptide that is secreted from the L cells of the gastrointestinal tract in response to food ("incretin response"). GLP-1 by acting thorough its receptor (GLP-1R), has potent effects on glucose-dependent insulin secretion, insulin gene expression, islet beta-cell neogenesis, gastrointestinal motility, energy homeostasis and food intake. The GLP-1 receptor (GLP-1R) is a member of the peptide hormone binding class B1 (secretin-like receptors) family of seven transmembrane spanning, heterotrimeric G-protein coupled receptors (GPCRs). GLP-1Rs have a broad distribution and they are found in the pancreas, adipose tissue, muscle, heart, the gastrointestinal tract and the liver. In addition, GLP-1Rs are found throughout the central nervous system (ie. hypothalamus, striatum, brain stem, substantia nigra, and subventricular zone), and there is some evidence that GLP-1R stimulation by GLP-1 exerts neuroprotective effects in both the central and peripheral nervous systems.

Human GLP-1 is a 37 amino acid residue peptide originating from preproglucagon which is synthesized i.a. in the L-cells in the distal ileum, in the pancreas and in the brain. The human preproglucagon is identified with the UniProt database Accesion Number P01275, Feb. 6, 2007; Version 3. The processing of preproglucagon to give GLP-1 (7-36) amide, GLP-1(7-37) and GLP-2 occurs mainly in the L-cells. A simple system is used to describe fragments and analogues of this peptide. Thus, for example, $Gly^8$-GLP-1 (7-37) designates a fragment (analogue) of GLP-1 formally derived from GLP-1 by deleting the amino acid residues Nos. 1 to 6 and substituting the naturally occurring amino acid residue in position 8 (Ala) by Gly. Similarly, $Lys^{34}(N^\epsilon$-tetradecanoyl)-GLP-1 (7-37) designates GLP-1(7-37) wherein the ε-amino group of the Lys residue in position 34 has been tetradecanoylated.

Particular analogues of GLP-1 include liraglutide (also named $Arg^{34}Lys^{26}(N^\epsilon$-(γ-glutamyl($N^\alpha$-hexadecanoyl)))-GLP-1 (7-37)) and with CAS number 204656-20-2 (SEQ ID NO: 1).

Lixisenatide is another GLP-1 analogue (i.e. a GLP-1 agonist) with amino acid sequence HGEGTFTSDL-SKQMEEEAVRLFIEWLKNGGPSSGAPPSKKKKKK$Xaa^1$, wherein $Xaa^1$ is a lysine residue in which the —COOH terminal has been modified (amidated) by a —NH2 group (in this description also disclosed as SEQ ID NO: 2). The CAS number is 827033-10-3.

Exenatide is the compound having the CAS number 141732-76-5. It is a peptide with the amino acid sequence HGEGTFTSDLSKQMEEEAVRLFIEW-LKNGGPSSGAPPPXaa$^1$, wherein Xaa$^1$ is a serine residue in which the terminal —COOH has been modified (amidated) by a —NH2 group (in this description also disclosed as SEQ ID NO: 3)

Preferred pharmaceutically or veterinary topical eye compositions are selected from the group consisting of solutions (for example eye drops), creams, lotions, unguents, emulsions, aerosols and non-aerosol sprays, gels, ointments and suspensions. As above exposed, the pharmaceutical or veterinary topical eye compositions are to be understood as topical eye compositions applicable to the cornea, sclera or to the conjunctival fornix.

These pharmaceutically or veterinary topical eye compositions also relate to solid or semi-solid matrices or supports, in particular bioerodible and/or biodegradable polymer matrices for the delivery of DPP-4 inhibitors, that are comprised in the matrices.

Additionally, the compositions of the present invention may contain other ingredients, such as fragrances, colorants, and other components known in the state of the art for use in topical eye formulations.

Topical eye compositions of the present invention can be prepared according to methods well known in the state of the art. The appropriate excipients and/or carriers, as well as any pH buffer, and their amounts, can readily be determined by those skilled in the art according to the type of formulation being prepared.

Examples of particular humectants (also named humectant solvents) are selected from the group consisting of polyethylene glycol (PEG of general formula H(OCH2CH2)nOH; wherein n is the mean of oxyethylene groups in the polymer), propylene glycol, glycerin, and mixtures thereof. In the context of the invention, the humectant is a compound having solvent and humectant properties.

PEG of different molecular weights are widely used in pharmaceutical compositions (being topical, parenteral, ophthalmicals, orals and rectal compositions). Appropriate PEGs to be used in the topical eye compositions for use according to the invention has a molecular weight from 300 to 35000 g/mol, more in particular from 600 to 20000 g/mol, even more in particular from 1000 to 8000 g/mol, more particularly from 3000 to 6000 g/mol, and preferably about 4000 g/mol.

In a particular embodiment of the compositions for use according to the invention, humectant is comprised in an amount from 1% to 49% in weight/volume in relation to the total volume of the composition. More in particular from 5% to 40%, even from 10% to 30%, and even more in particular from 15% to 25%.

Excipients used as pH buffers are those allowing a pH from 4.5 to 9.0, more in particular from 4.5 to 8.5, even more in particular from 6.0 to 8.2, and preferably from 7.0 to 8.1, even more preferably from 7.5 to 8.0. Examples of pH buffers include citrate salts (citric acid/citrate buffer), phosphate salts (phosporic acid/phosphate buffer), borate salts (boric acid/borate buffer), and mixtures thereof, all salts being those pharmaceuticaly acceptable. pH buffers may in additional comprise amino acids, in particular arginine, lysine, and an amine-derived compound selected from methylglucamine and trometamol, and mixtures thereof.

Excipients and/or carriers, more appropriate for lipophilic compositions (which means compositions non miscible with water at 15-35° C.) include synthetic or semisynthetic lipophilic excipients comprising cocoa butter, vegetal hydrogenated oils and solid semisynthetic glycerides.

Other components in the topical eye (ophthalmic) composition of the invention include, in particular embodiments, tensoactives, solvents (organic and inorganic solvents; i.e. water), viscosity agents, preservatives, agglutinants, emollients, and antioxidants, isotonifying and/or isoosmozing agents, mucoadhesive polymers, agent enhancing absorption of the active principle (i.e.: DPP-4 inhibitor). Among the tensoactives, are in particular used glycerides, polysorbates, sodium lauryl sulphate, phospholipids, (such as phosphatidyl choline or phosphatidyl glycerol), polyoxyethylene fatty acids, mono-di and triglycerides, optionally polyoxyethylene substituted, and mixtures thereof.

Among the organic solvents, are particularly used in the compositions ricin oil, PEG, poloxamers, polysorbates, glycerine, triglycerides with C6-C10 carbon atoms fatty acids, and mixtures thereof.

The viscosity agents are in particular polyvinyl alcohol, compounds derived from cellulose such as methylecellulose and hydroxypropylmethylcellulose, carbomers, PEG and mixtures thereof. The preservatives are in particular boric acid, benzalconium chloride, benzoic acid, p-hydroxybenzoic esters of C1-C4-alkyl chains, chlorobuthanol, benzyl alcohol, and mixtures thereof.

Isotonifying and/or isoosmozing agents, are in particular sodium chloride, dextrose, trehalose, mannitol, amino acids and mixtures thereof. Agents enhancing absorption of the active principle include saponine, fatty acids, pyrrolydone, polyvinylpyrrolidone, pirivic acid and mixtures thereof. The mucoadhesive polymers (used commonly as gelifying anegnts) are in particular hyaluronic acid, polygalacturonic acid, polyacrylic acid, chondroitin sulphate, methylecellulose, hydroxypropylmethylcellulose, gelatine, methycellulose, chantan gum, sodium carboxymethylcellulose, chitosan, carbopol, gellan gum, pectine, algunates, carragenates, and mixtures thereof.

Emulsion and microemulsion bases are in particular fatty acid esters of glycerine, polyoxyethylene alcohols, ricin oil, triglycerides with C6-C10 carbon atoms fatty acids, and mixtures thereof.

Cream and ointment bases are in particular vaseline, paraffin, PEG, silicones and mixtures In a preferred embodiment, optionally in combination with any embodiments above or below, the topical eye composition of the invention is a solution in the form of eye drops, also named eye drop solution. The administration of the peptides in the form of eye drops implies the great advantage of being easy to be used by the subject in need thereof, and non-uncomfortable.

The compositions for use according to the invention are, in a particular embodiment optionally in combination with any embodiment above or below, sustained-release compositions. That is, the compositions are formulated as sustained-release delivery systems allowing the delivery of the active principle (i.e.: DPP-4 inhibitors) at a predetermined rate in order to maintain a constant drug concentration for a specific period of time with minimum side effects.

Particular formulations for the sustained-release delivery comprise nanoparticles and microparticles encapsulating the DPP-4 inhibitor, liposomes and niosomes, all of them comprising a compound selected from polylactic acid, poly(lactic-co-glycolic) acid, polystyrenes, chitosan, albumin, lectins, gelatins, acrylates and methacrylates, polycaprolactones, polyacrylamides, dextranes, agarose, sorbitan, cholesterol, and mixtures thereof. Other Particular formulations for the sustained-release delivery comprise a polymer conjugated with the DPP-4 inhibitors constituting hydrogels.

All these pharmaceutical or veterinary topical eye compositions are, in another particular embodiment of the second aspect optionally in combination with any embodiments above or below, for use in the topical eye treatment and/or prevention of retinal neurodegenerative diseases selected from the group consisting of diabetic retinopathy (DR), age-related macular degeneration, glaucoma and retinitis pigmentosa. In particular, they are for use in the prevention and/or treatment of diabetic retinopathy, and its associated microvascular impairment or damage. More in particular, they are for use in the topical eye treatment of early stages of the diabetic retinopathy.

As indicated, the invention has as another aspect, a pharmaceutical or veterinary topical composition comprising a therapeutically effective amount of a DPP-4 inhibitor, or a pharmaceutically or veterinary acceptable salt thereof, together with topical pharmaceutically or veterinary acceptable excipients and/or carriers, wherein the composition has a dynamic viscosity from $5.0 \times 10^{-4}$ Pa·s to 300 Pa·s, a pH from 4.5 to 9.0, and wherein the dipeptidyl peptidase-4 inhibitor is in a concentration from 5 mg/ml to 200 mg/ml in relation to the final volume of the composition.

More in particular, a pharmaceutical or veterinary topical composition comprising a therapeutically effective amount of a DPP-4 inhibitor, or a pharmaceutically or veterinary acceptable salt thereof, together with topical pharmaceutically or veterinary acceptable excipients and/or carriers, wherein the composition has a dynamic viscosity from $5.0 \times 10^{-4}$ Pa·s to 300 Pa·s at 20° C., a pH from 4.5 to 9.0, and wherein the dipeptidyl peptidase-4 inhibitor is in a concentration from 20 mg/ml to 200 mg/ml in relation to the final volume of the composition.

Indeed, the pharmaceutical or veterinary topical eye compositions of the invention are liquid compositions or semi-solid compositions having a consistency of that of a cream or an unguent.

When in this description it is indicated that a composition has a particular viscosity within a range, it is related to the dynamic viscosity. Thus, the pharmaceutical or veterinary topical compositions of the invention have a dynamic viscosity from $5.0 \times 10^{-4}$ Pa·s to 300 Pa·s, at room temperature (i.e. 20±0.1° C.) and normal atmospheric pressure. In a particular embodiment of this third aspect, the dynamic viscosity of the pharmaceutical or veterinary topical composition is from $8.9 \times 10^{-4}$ Pa·s to 100 Pa·s According to the European pharmacopoeia (8th edition, 2.2.8 "Viscosity"), dynamic viscosity or viscosity coefficient $\eta$ is the tangencial force per unit surface, known as shearing stress T and expressed in pascals, necessary to move, parallel to the sliding plane, a layer of liquid of 1 square meter at a rate (v) of 1 meter per second relative to a parallel layer at a distance (x) of 1 meter. The ratio dv/dx is a speed gradient giving the rate of shear D expressed in reciprocal seconds ($s^{-1}$), so that $\eta=T/D$. The unit of dynamic viscosity is the pascal second (Pa·s).

All excipients and/or carriers, and buffers mentioned before apply to this other aspect.

In particular, these topical compositions with the specified viscosity are in the form of solutions (for example eye drops), creams, lotions (for example eye lotions), unguents, emulsions, aerosols and non-aerosol sprays, gels, ointments and suspensions. All of them can be applied onto the surface of the eye (cornea, conjunctiva, sclera) and allow DPP-4 inhibitors release to reach the retina. Particular compositions are eye drops, eye lotions, semi-solid eye preparations (i.e. ointments, creams or gels). Some of the eye solutions end lotions can be prepared at the time of administration from powders of eye drops and powders for eye lotions, supplied in a dry, sterile form to be dissolved or suspended in an appropriate liquid vehicle.

More in particular, DPP-4 inhibitors are, as before, selected from the group consisting of sitagliptin, saxagliptin, vildagliptin, linagliptin, anagliptin, teneligliptin, alogliptin, trelagliptin, gemigliptin, omarigliptin and mixtures thereof, together with topical pharmaceutically or veterinary acceptable excipients and/or carriers.

In another particular embodiment of the pharmaceutically or veterinary topical eye compositions of the invention, pH is from 5.5 to 7.5, more particularly 7.0.

In yet another particular embodiment of the pharmaceutically or veterinary topical eye compositions of the invention, the DPP-4 inhibitor is in a concentration from 50 mg/ml to 150 mg/ml in relation to the final volume of the composition. More particularly the concentration is from 50 mg/ml to 150 mg/ml.

Yet more in particular, if the inhibitor is saxagliptin, it is in a concentration from 80 mg/ml to 120 mg/ml in relation to the final volume of the composition. More particularly the concentration is from 80 mg/ml to 100 mg/ml in relation to the final volume of the composition. Particularly, it is 100 mg/ml in relation to the final volume of the composition.

Yet more in particular, if the inhibitor is sitagliptin, it is in a concentration from 50 mg/ml to 120 mg/ml in relation to the final volume of the composition. More particularly the concentration is from 50 mg/ml to 80 mg/ml in relation to the final volume of the composition. Particularly, it is 50 mg/ml in relation to the final volume of the composition.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1. DPP-4 Concentration are Elevated in Human Diabetic Retinas

The expression of DPP-4 were determined in human retinas from diabetic and non-diabetic donors. Retinas were obtained from Tissue Bank of our Centre (Banc de Sang i Teixits Hospital Universitari Vall d'Hebron). A total of 8 diabetic donors and 8 non-diabetic donors matched by age and gender were included in the study. One eye-cup was harvested in order to separate neuroretina from retinal pigment epithelium (RPE) and both tissues were immediately frozen with liquid nitrogen and stored at −80° C. Tissues derived from this eye-cup were used for the studies of gene expression and measurements of proteins. The other eye-cup was also harvested and both RPE and neuroretina were soaked in paraffin and were used for performing immunohistochemical studies. The time period from death to eye enucleation was 3.7±1.5 h.

The procedure for eye-cup donation and for the handling of this biologic material is rigorously regulated by the protocol of donations of the Tissue Bank of our Centre and has been approved by the ethical committee.

RNA Extraction and Quantitative RT-PCR:

Total RNA was extracted using TRIzol® reagent (Invitrogen, Madrid, Spain). Then, RNA samples were treated with DNAse (Qiagen, Madrid, Spain) to remove genomic contamination and purified on an RNeasy MinElute column (Qiagen, Madrid, Spain). RNA quantity was measured on a Nanodrop spectrophotometer, and integrity was determined on an Agilent 2100 Bioanalyzer. Reverse transcription was performed with a High Capacity kit (Applied Biosystems, Madrid, Spain) with random hexamer primers. The real-time PCR was performed using primers for DPP-4.

DPP-4 Protein Measurement:

DPP-4 concentration was assessed in retinal extracts (RPE and neuroretina) by a quantitative sandwich enzyme immunoassay (R&D Systems, Minneapolis, Minn.) with a lower limit of detection of 0.016 ng/mL.

Immunohistochemistry

Retinal sections of eye human donors (8 non-diabetic and 8 diabetic donors) were deparaffinized in xilol and rehydrated in graded ethanol. To eliminate autofluorescence, slides were washed in protassium permanganate. Then, sections were incubated for 1 h in 2% BSA 0.05% Tween in PBS to block unspecificities. Primary antibody was incubated overnight at 4° C. in the same blocking buffe (1:500; Abcam, Cambridge, UK). Then, sections were washed and incubated with Alexa Fluor® 488 (Molecular Probes, Eugene, Oreg.) at room temperature for 1 h. Slides were coverslipped with a drop of mounting medium containing DAPI for visualization of cell nuclei (Vector Laboratories, Burlingame, Calif.). Images were acquired with a confocal laser scanning microscope (FV1000, Olympus. Hamburg, Germany) at 40× using the 488 nm and 405 nm laser lines and each image was saved at a resolution of 1024×1024 pixels.

Results:

DPP-4 was expressed in human retina. A higher expression of DPP-4 mRNA was detected in the RPE from diabetic donors in comparison with non-diabetic donors (5.69±1.77 vs. control 1.4±1.38, $p<0.05$). In the neuroretina no significant differences between the two groups were observed.

DPP-4 concentration was significantly higher in RPE from diabetic donors in comparison with non-diabetic donors ($p<0.05$). All these data are depicted in FIG. 1, wherein levels of DDP-4 (ng/ml) are shown in bowel (reference), liver (reference), RPE and neuroretina. White bars: non-diabetic donors. Black bars: diabetic donors. In the neuroretina no significant differences between the two groups were observed. The immunohistochemistry analysis showed that DPP-4 was diffusely distributed along the entire retina.

Example 2. Saxagliptin Administered in Eye Drops Prevents Retinal Neurodegeneration Induced by Diabetes The neuroprotective effect of eye-drops containing saxagliptin were tested in the db/db mouse model. It has been reported that db/db mice reproduce the features of the neurodegenerative process that occurs in the human diabetic eye. Therefore, it is an appropriate model for testing neuroprotective drugs (according to Bogdanov et al., "The db/db mouse: a useful model for the study of diabetic retinal neurodegeneration", *PLoS One*—2014, vol. no. 9(5): e97302). A total of 20 male db/db (BKS.Cg-+Lepr db/+Lepr db/OlaHsd) mice aged 10 weeks were purchased from Harlan Laboratories, Inc. In addition, 10 non-diabetic (db/+) mice matched by age were used as control group.

Saxagliptin or vehicle eye drops were administered directly onto the superior corneal surface of each eye using a syringe. One drop (5 μL) of saxagliptin (1 μM) to each eye or vehicle (5 μL of 0.9% sodium chloride) to each eye were administered twice daily for 14 days. On day 15, the animals' eyes were instilled with a drop of saxagliptin or vehicle approximately one hour prior to necropsy. This study was approved by the Animal Care and Use Committee of VHIR (Vail d'Hebron Research Institute). All the experiments were performed in accordance with the tenets of the European Community (86/609/CEE) and ARVO (Association for Research in Vision and Ophthalmology).

Full field electroretinography (ERG) recordings were measured using the Ganzfeld ERG platform (Phoenix Research Laboratories, Pleasanton, Calif.) following ISCEV (International Society for Clinical Electrophysiology of Vision) recommendations (according to Marmor et al., "Standard for clinical electroretinography.", International Society for Clinical Electrophysiology of Vision (2004), *Doc Ophthalmol*—2004; vol. 108, pp.: 107-114).

Neurodegeneration Measurements:

(A) Measurements of Glial Activation

Glial activation was evaluated by Laser Scanning Confocal microscopy using specific antibodies against GFAP (Glial fibrillar acidic protein). Sections were fixed in acid methanol (−20° C.) for 2 min, followed by three washes with PBS, 5 min each. Sections were permeabilized with TBS-Triton X-100 0.025% and were incubated in blocker (1 BSA, and 10% goat serum in PBS) for 2 hours at room temperature. Sections were then incubated with rabbit anti-GFAP (Abcam Ltd, Cambridge, U.K.) (1:500 dilution prepared in blocking solution) overnight at 4° C. in a humid atmosphere. After three washes in PBS, 5 min each, the sections were incubated with secondary antibody Alexa 488 goat-anti-rabbit (Invitrogen) (1:200 dilution prepared in blocking solution). The sections were washed three times in PBS, counterstained with Hoestch and mounted with Mounting Medium Fluorescence (Prolong, Invitrogen) and mounted with a coverslip. Comparative digital images from samples were recorded with a Fluoview FV 1000 Laser Scanning Confocal Microscope Olympus using identical brightness and contrast settings.

To evaluate the degree of glial activation it was used a scoring system based on the extent of GFAP staining previously described (Anderson et al., "Glial and endothelial blood-retinal barrier responses to amyloid-beta in the neural retina of the rat", *Clin Ophthalmol*—2008, vol. no. 2, pp.: 801-816). This scoring system was as follows: Müller cell endfeet region/GCL only (score 1); Müller cell endfeet region/GCL plus a few proximal processes (score 2); Müller cell endfeet plus many processes, but not extending to ONL (score 3); Müller cell endfeet plus processes throughout with some in the ONL (score 4); Müller cell endfeet plus lots of dark processes from GCL to outer margin of ONL (score 5).

(B) Immunohistochemical Analysis for Apoptosis Assessment

The TUNEL (Terminal Transferase dUTP Nick-End Labeling) staining was carried out using the DeadEnd Fluorometric TUNEL System kit (PROMEGA, Madison, Wis., USA). Cryosections of retina were permeabilised by incubation for 2 min on ice with 0.1% Triton X-100 in 0.1% sodium citrate, freshly prepared. The secondary antibody was Alexa 488 goat-anti-rabbit (Invitrogen, San Diego Calif., USA). For evaluation by Laser Scanning Confocal microscopy the excitation wavelength was 488 nm and detection in the range of 515-565 nm (green) was used.

(C) Glutamate Quantification

Quantification of glutamate was performed by reverse phase ultra-performance liquid chromatography (UPLC) (Acquity-UPLC, Waters) as aminoquinoline derivatives (AccQ-Tag chemistry, MassTrak AAA method and instruments, Waters, Milford, Mass.).

(D) Immunohistochemistry for GLAST

GLAST (glutamate-aspartate transporter), the main glutamate transporter, was evaluated by fluorescence microscopy using specific antibodies. GLAST was evaluated by fluorescence microscopy using specific antibodies [rabbit anti-GLAST (EAAT1) (1:100, Abcam ab416, Cambridge, UK).

Glutamate accumulation in extracellular space and the overactivation of glutamate receptors ("excitotoxicity") plays an important role in retinal neurodegeneration. Glutamate transporters are essential for keeping the extracellular glutamate concentration below neurotoxic levels. Glutamate/aspartate transporter (GLAST) is the most dominant glutamate transporter, accounting for at least 50% of glutamate uptake in the mammalian retina.

Results

Blood glucose concentration and body weight at the end of treatment were similar in db/db mice treated with saxagliptin eye drops than in db/db mice treated with vehicle.

(A) Retinal Neurodegeneration was Prevented in Diabetic Mice Treated with Saxagliptin:

Glial Activation

In non-diabetic mice GFAP expression was confined to the retinal ganglion cell layer (GCL) and therefore the GFAP score was ≤2. The diabetic mice treated with vehicle (D-Sham) presented significant higher GFAP expression than non-diabetic mice matched by age (C (db/+)). Thus, 100% of diabetic mice presented a GFAP score 3. Saxagliptin (eye drops) administration for two weeks (D-saxagliptin) resulted in a significant decrease of reactive gliosis, and the GFAP score of the mice treated with saxagliptin was <3 in all cases. All these data are derivable from digital images (not shown) with Fluoview FV 1000 Laser Scanning Microscope showing Glial Fibrillar Acidic Protein (GFAP) immunofluorescence (in green) between representative samples from a db/db mouse treated with vehicle (D-Sham), a db/db mouse treated with saxagliptin (D-SAXAGLIPTIN), and a non-diabetic mouse (c(db/+)). Nuclei were labeled with Hoechst (blue), and outer nuclear layer (ONL), inner nuclear layer (INL); and ganglion cell layer (GCL) were clearly viewed.

For the sake of understanding, next table 1 shows the percentage (%) of positive GFAP labeling:

TABLE 1

| | % positive GFAP labeling | | |
|---|---|---|---|
| score | D-Sham | D-SAXAGLIPTIN | db/+ |
| 1 | 0.00 | 95.00 | 95.00 |
| 2 | 0.00 | 5.00 | 5.00 |
| 3 | 65.00 | 0.00 | 0.00 |
| 4 | 30.00 | 0.00 | 0.00 |
| 5 | 5.00 | 0.00 | 0.00 |

This Table 1 shows quantification of glial activation based on the extent of GFAP staining. The scoring system was as follows: Müller cell endfeet region/GCL only (score 1); Müller cell endfeet region/GCL plus a few proximal processes (score 2); Müller cell endfeet plus many processes, but not extending to ONL (score 3); Müller cell endfeet plus processes throughout with some in the ONL (score 4); Müller cell endfeet plus lots of dark processes from GCL to outer margin of ONL (score 5). n=10 mice per group (5 retinal sections per mice).

Retinal Apoptosis

Figure 2:
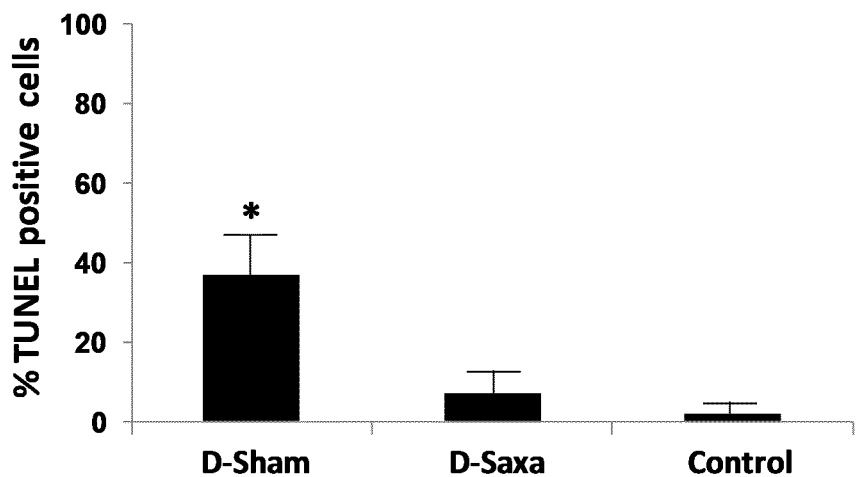
FIG. 2 is a graphic with the percentage of TUNEL positive cells in the retinal layers. The percentage of Terminal Transfer dUTP Nick-End Labeling (TUNEL) positive cells for showing apoptosis was significantly higher ($p<0.001$) in db/db mice treated with vehicle (D-Sham) in comparison with the other groups (D-saxa and Control) in all retinal layers (Outer nuclear layer; ONL, inner nuclear layer; INL, and Ganglion cell lay; GCL). N=10 mice per group (minimum 10 sections per retina). Saxa: saxagliptin.

The apoptosis rate was significantly higher in diabetic mice treated with vehicle than in non-diabetic mice in all retinal layers. Saxagliptin (eye drops) administration for two weeks resulted in a significant prevention of apoptosis in all retinal layers, as derivable from FIG. 2, a bar-graphic with the percentage (%) of TUNEL positive cells for D-Sham mice (diabetics and non-treated, to which vehicle was administered to each eye), D-Saxa (diabetics and receiving the Saxagliptin drops) and Control (non-diabetic).

Figure 3:
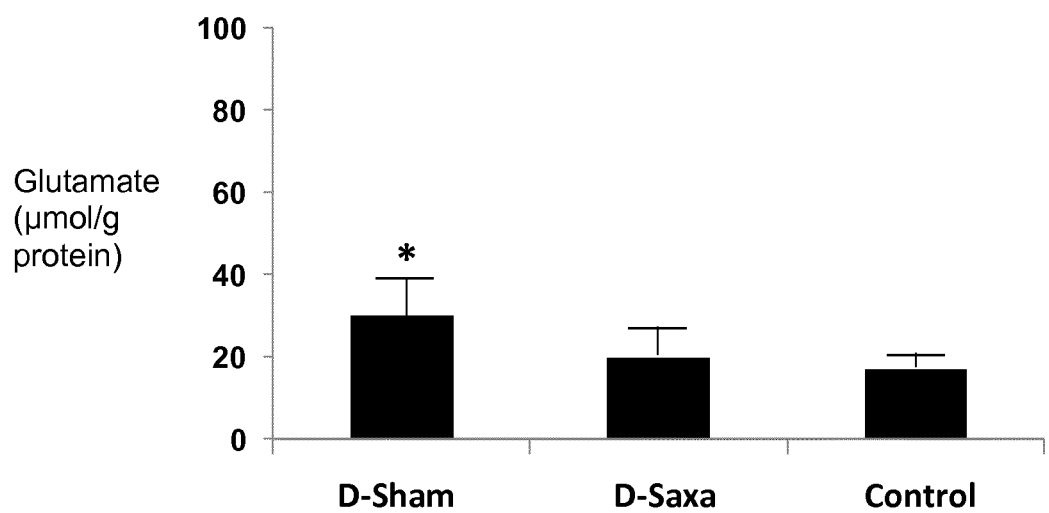
FIG. 3 is a graphic with bars with the retinal concentration of glutamate (µmol/g protein) in the investigational groups. *$p<0.05$ in comparison with the other groups. Saxa: saxagliptin.

(B) Saxagliptin Administration Prevents the Increase of Glutamate Induced by Diabetes Glutamate levels (μmol/g protein) in the diabetic retinas were higher than in non diabetic retinas. In diabetic mice treated with saxagliptin, glutamate concentration was significantly lower in comparison with diabetic mice treated with vehicle (p<0.05) and similar to control mice (p=n.s). Data are shown in FIG. 3 for controls, D-Sham mice and S-Saxa mice, with the same meaning as before.

Explaining this finding, it was observed that glutamate/aspartate transporter (GLAST), the main glutamate transporter expressed by Müller cells, was significantly decreased in the retinas of diabetic mice treated with vehicle (D-Sham) in comparison with non-diabetic mice (Control db/+), as was depicted in digital images (not shown) with Fluoview FV 1000 Laser Scanning Microscope showing Glutamate Aspartate transporter (GLAST) immunofluorescence (in red) between representative samples from a db/db mouse treated with vehicle (D-Sham), a db/db mouse treated with saxagliptin (D-SAXAGLIPTIN) and a non-diabetic mouse (Control (db/+)). Nuclei were labeled with Hoechst (blue).

In diabetic mice treated with saxagliptin (D-SAXAGLIPTIN) this downregulation of GLAST induced by diabetes was prevented, thus also showing red staining and resembling the control image.

Figure 4:
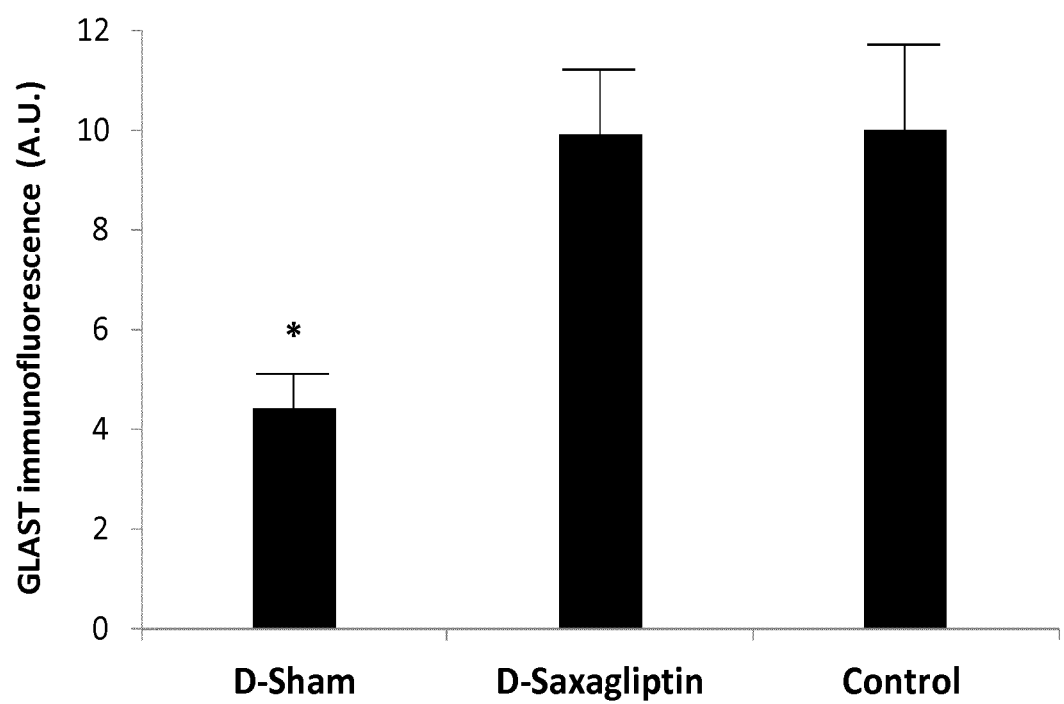
FIG. 4 is a graphic with bars with quantification of GLAST immunofluorescence in arbitrary units (A.U.). n=10 mice per group. Results are the mean±SD. *$p<0.05$ between db/db treated with vehicle (D-Sham) and the other groups (D-SAXAGLIPTIN and Control (db/+)).

All these data are herewith depicted in FIG. 4, wherein quantification of GLAST immunofluorescence in arbitrary units (A.U.) is shown. n=10 mice per group. Results are the mean±SD. *p<0.05 between db/db treated with vehicle (D-Sham) and the other groups(D-Saxagliptin and Control (db/+).

(C) Topical Administration of Saxagliptin Prevents the Disruption of the Blood-Retinal Barrier (BRB)

In order to assess the effect of saxagliptin on early microvascular impairment the albumin leakage was examined. Higher extravasation of albumin (was observed in db/db mice treated with vehicle (D-Sham) in comparison with control animals (C db/+). Treatment with saxagliptin (D-SAXAGLIPTIN, eye drops) prevented albumin leakage in db/db/mice.

Figure 6:
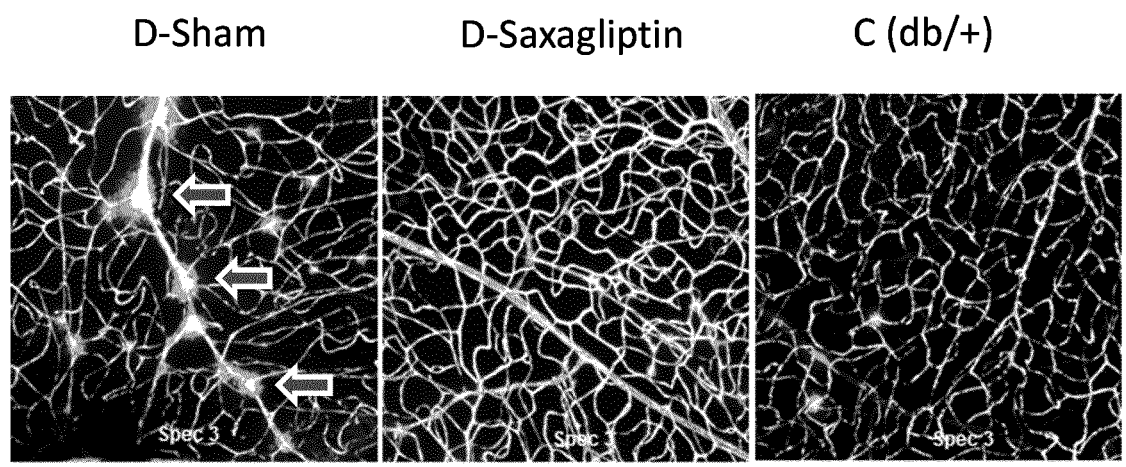
FIG. 6 (A) shows vascular leakage of serum albumin-bound Evans blue visualized with a laser scanning confocal microscope. The number and extent of Evans blue-albumin complex leakage is visualized and signalized with arrows in D-Sham. In the lower panel, FIG. 6(B), the quantification of albumin immunofluorescence of digital images with Fluoview FV 1000 Laser Scanning Microscope is shown in arbitrary units (A.U.). Results are the mean±SD. *$p<0.05$ between db/db treated with vehicle (D-Sham) and the other groups: D-Saxagliptin and C(db/+).
Figure 6:
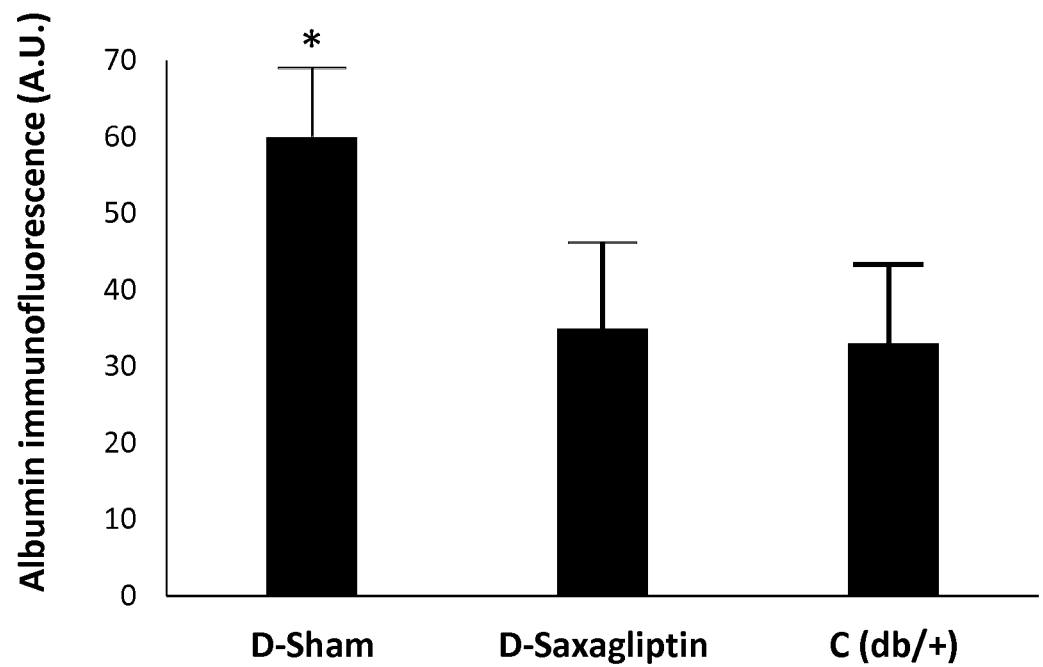

FIG. 6 (A) shows vascular leakage of serum albumin-bound Evans blue visualized with a laser scanning confocal microscope. The number and extent of Evans blue-albumin complex leakage (arrows) were clearly increased in D-Sham than in the other groups. In the lower panel FIG. 6(B) the quantification of albumin immunofluorescence of digital images with Fluoview FV 1000 Laser Scanning Microscope is shown. Immunohistochemistry images of Fluoview FV 1000 Laser Scanning Microscope from which quantification of albumina (in red) was done are not shown. The three type of samples tested were: D-Sham, D-SAXAGLIPTIN and C (db/+). Results are the mean±SD. *p<0.05 between db/db treated with vehicle (D-Sham) and the other groups.

(D) Saxagliptin Treatment Prevents ERG Abnormalities Induced by Diabetes

Figure 5:
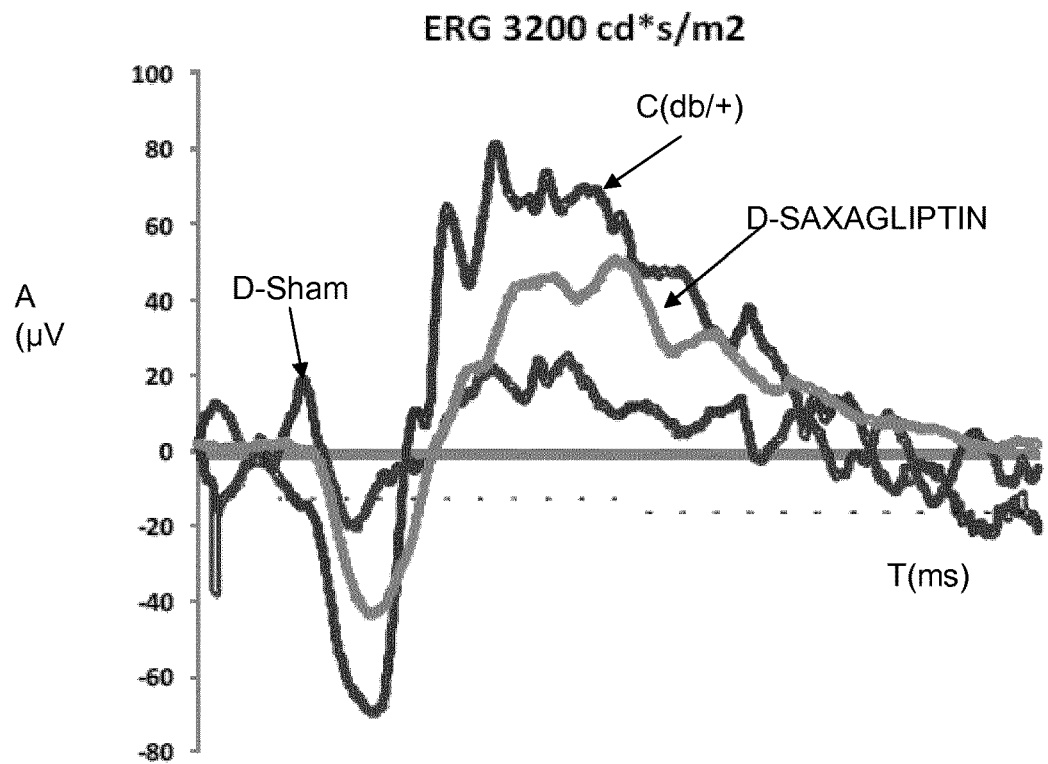
FIG. 5 depicts electroretinography (ERG) traces in response to stimulus intensity of 3200 candela (cd)s/m² (panel A) and 12800 candela (cd)s/m² (panel B) in a representative non-diabetic mouse (C(db/+)), a db/db mouse treated with vehicle (D-Sham), and a db/db mouse treated with saxagliptin (D-SAXAGLIPTIN). A means amplitude and is measured in microvolts (μV); T means time in milliseconds (ms).
Figure 5:
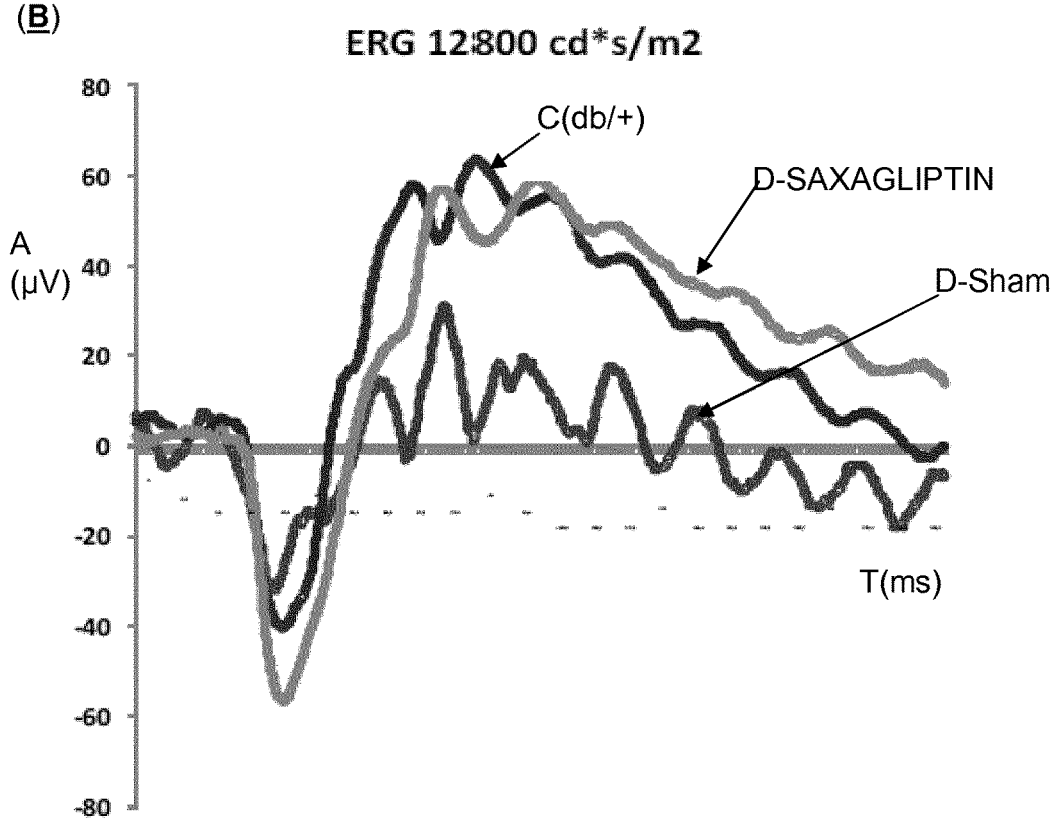

Treatment with saxagliptin topically administered onto the eye prevented the reduction of a-wave and b-wave amplitude induced by diabetes, as well as the increase of a-wave and b-wave implicit time. Data are depicted in FIG. 5, wherein the Electroretinograms (ERG) at 3200 cd*s/m$^2$ (panel A) and at 12800 cd*s/m$^2$ (panel B) are represented for D-sham mice (diabetics treated with vehicle eye drops), Controls (C; d/+) and D-saxagliptin mice (diabetics treated with Saxagliptin eye drops). A means amplitude and is measured in microvolts (μV); T means time in milliseconds (ms).

Example 3. Sitagliptin Topically Administered (Eye Drops) Prevents Retinal Neurodegeneration Induced by Diabetes The design and methodology were the same than used in Example 2. The results obtained using sitagliptin eye drops were very similar to than obtained with saxagliptin eye drops treatment.

Blood glucose concentration and body weight at the end of treatment were similar in db/db mice treated with sitagliptin eye drops (S-sitagliptin) than in db/db mice treated with vehicle (D-Sham).

Glial Activation

Sitagliptin (eye drops) administration for two weeks resulted in a significant decrease of reactive gliosis, and the GFAP score of the mice treated with sitagliptin was ≤3 in all cases, as derived from data in Table 2.

TABLE 2

| Score | D-Sham | D-Sitagliptin (eye drops) | control (db/+) |
|---|---|---|---|
| 1 | 0.00 | 85.00 | 100.00 |
| 2 | 0.00 | 10.00 | 0.00 |
| 3 | 35.00 | 5.00 | 0.00 |
| 4 | 50.00 | 0.00 | 0.00 |
| 5 | 15.00 | 0.00 | 0.00 |

Retinal Apoptosis

Figure 7:
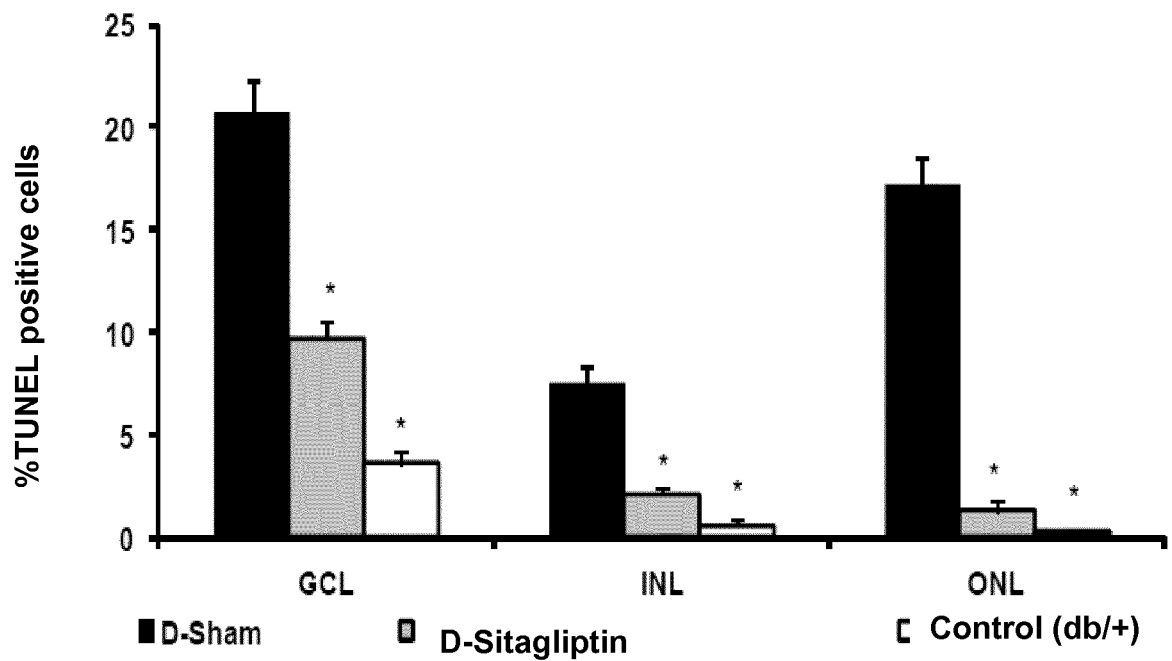
FIG. 7, related with Example 3, shows the percentage of TUNEL positive cells in the retinal layers in db/db mice treated with vehicle (D-Sham) in comparison with the other groups (D-sitagliptin and Control (db/+)) in all retinal layers (*$p<0.01$). ONL: outer nuclear layer; INL: inner nuclear layer; GCL: ganglion cell layer. N=10 mice per group (minimum 10 sections per retina).

The apoptosis rate was significantly higher in diabetic mice treated with vehicle than in non-diabetic mice in all retinal layers. Sitagliptin (eye drops) administration for two weeks resulted in a significant prevention of apoptosis in all retinal layers, as derivable from FIG. 7, a bar-graphic with the percentage (%) of TUNEL positive cells for D-Sham mice (diabetics and receiving vehicle eye-drops; black bars on the left of each set), D-Sitagliptin (receiving the Sitagliptin drops; grey bars in the middle of each set) and Control (db/+). Data for the different retina layers (ganglion cell layer; GCL, inner nuclear layer; INN, and outer nuclear layer; ONL) are depicted. The percentage of TUNEL positive cells was significantly higher in db/db mice treated with vehicle in comparison with the other groups in all retinal layers (*p<0.01). ONL: outer nuclear layer; INL: inner nuclear layer; GCL: ganglion cell layer. N=10 mice per group (minimum 10 sections per retina).

Figure 8:
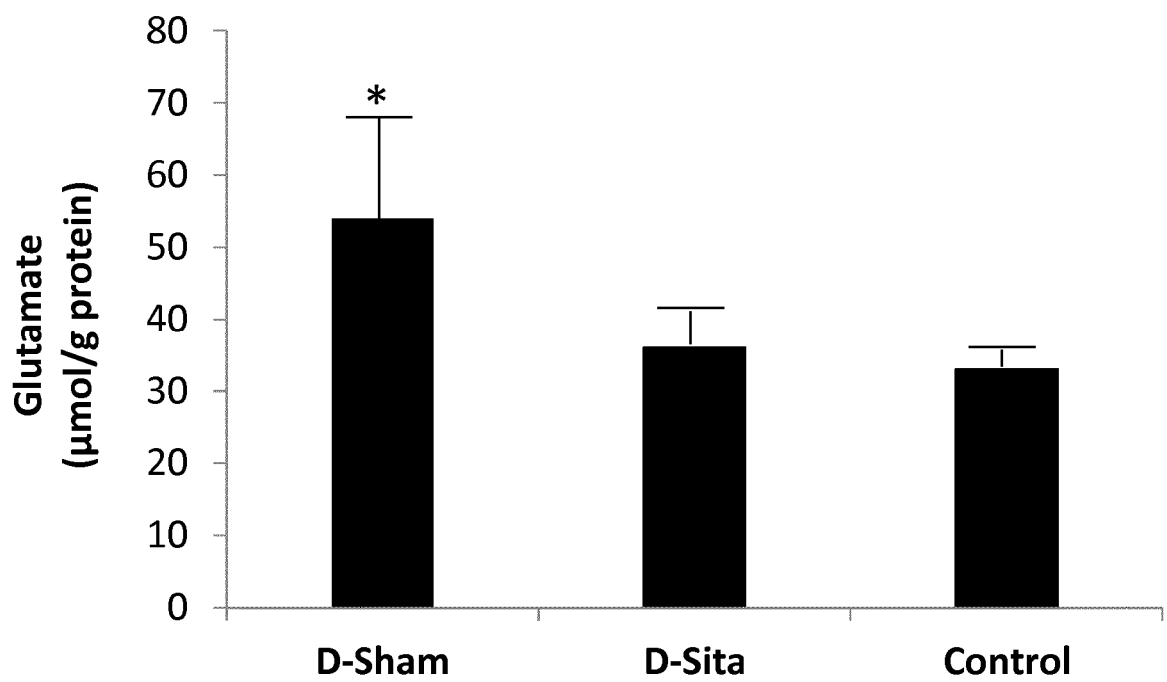
FIG. 8 is a graphic with bars with the retinal concentration of glutamate (μmol/g protein) in the investigational groups. *$p<0.05$ in comparison with the other groups. Sita: sitagliptin.

Sitagliptin treatment (eye drops) also prevented glutamate accumulation by abrogating the downregulation of GLAST induced by diabetes in the same way as Saxagliptin (FIG. 8). In addition, sitagliptin also prevented functional abnormalities measured by ERG.

Figure 9:
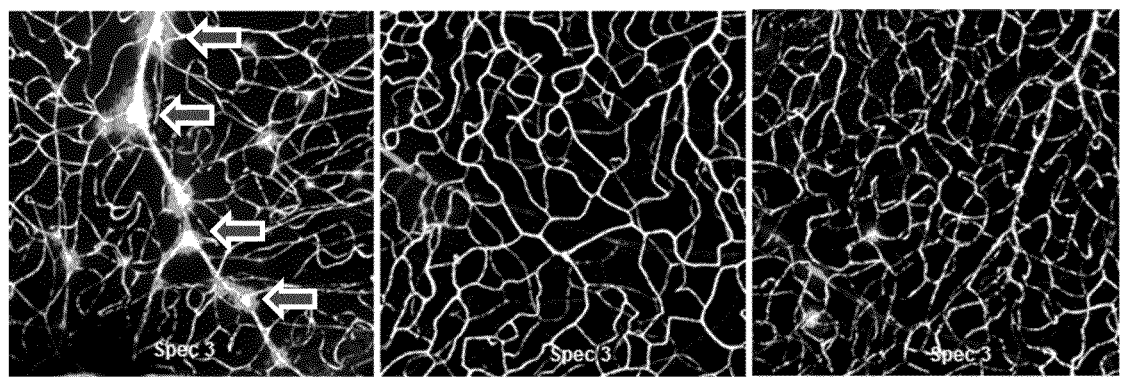
FIG. 9 (A) shows vascular leakage of serum albumin-bound Evans blue visualized with a laser scanning confocal microscope. The number and extent of Evans blue-albumin complex leakage is visualized and signalized with arrows in D-Sham. In the lower panel, FIG. 9(B), the quantification of albumin immunofluorescence of digital images with Fluoview FV 1000 Laser Scanning Microscope is shown in arbitrary units (A.U.). Results are the mean±SD. *$p<0.05$ between db/db treated with vehicle (D-Sham) and the other groups: D-Sitagliptin and C(db/+).
Figure 9:
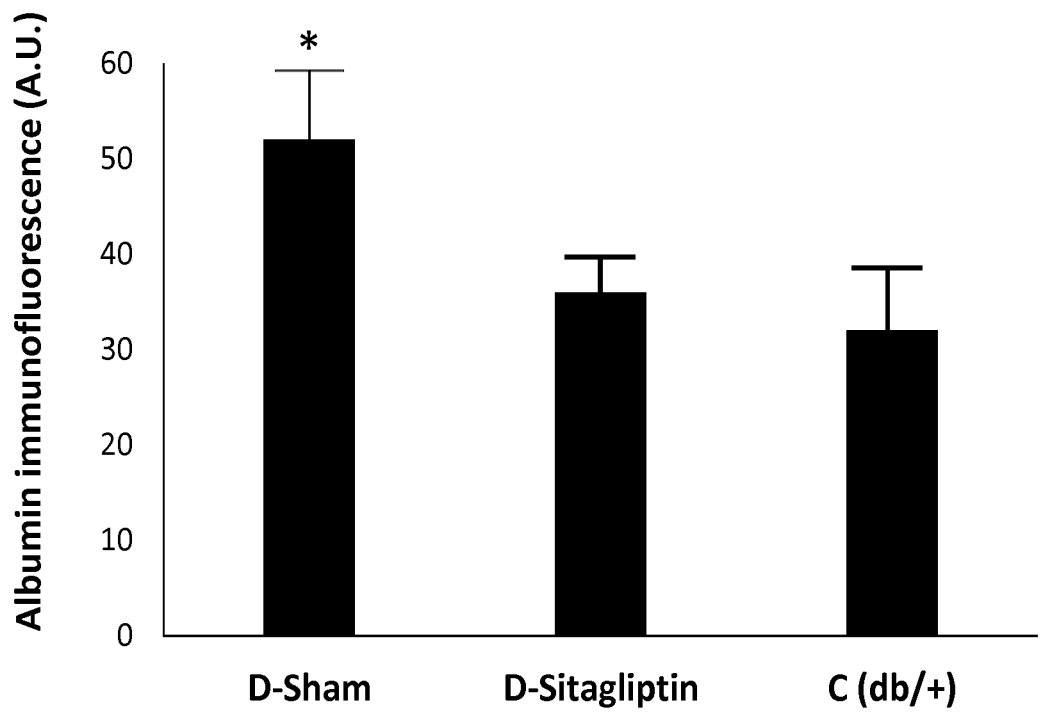

Finally, sitagliptin also preserved the sealing function of the BRB. FIG. 9(A) shows vascular leakage of serum albumin-bound Evans blue visualized with a laser scanning confocal microscope. The number and extent of Evans blue-albumin complex leakage (arrows) were clearly increased in D-Sham than in the other groups. In the lower panel FIG. 9(B) the quantification of albumin immunofluorescence of digital images with Fluoview FV 1000 Laser Scanning Microscope is shown. Immunohistochemistry images of Fluoview FV 1000 Laser Scanning Microscope from which quantification of albumina (in red) was done are not shown. The three type of samples tested were: D-Sham, D-Sitagliptin and C (db/+). Results are the mean±SD. *p<0.05 between db/db treated with vehicle (D-Sham) and the other groups.

Extravasation of albumin was observed in db/db mice treated with vehicle (D-Sham) in comparison with control animals (C db/+). Treatment with sitagliptin (D-Sitagliptin, eye drops) prevented albumin leakage in db/db/mice.

It is to be noted that all these effects of saxagliptin and sitagliptin eye drops were observed without any change in blood glucose levels and, therefore, they cannot be attributed to changes in the diabetic milieu. However, activation of other pathways unrelated to GLP-1 receptor cannot be ruled out.

Although data not shown, DPP-4 inhibitors (saxagliptin and sitagliptin) administered by eye drops led to a significant increase in the intraretinal content of GLP-1 and its main downstream messenger cAMP, thus preventing neurodegeneration and vascular leakage in db/db mice. This does not mean that the beneficial effects of DPP-4 inhibitors should exclusively be attributed to the enhancement of GLP-1. Without being bound to any theory, inventors consider that, in fact, the DPP-4 inhibitors themselves activate unrelated downstream GLP-1R pathways that might be involved in neuroprotection.

In this regard, Dietrich et al. [Dietrich N, Kolibabka M, Busch S, et al (2016) *The DPP4 Inhibitor Linagliptin Protects from Experimental Diabetic Retinopathy. PLoS One* 11:e0167853] recently reported that linagliptin (a DPP-4 inhibitor) has neuroprotective effect in *C. Elegans*, a model of neurodegeneration induced by high glucose levels which do not express GLP-1R. Also, it should be noted that G-protein-coupled receptor (GPcR) coagulation factor II receptor-like 1 (F2rl 1, previously known as Par2), which is abundant in retinal ganglion cells, can be activated by DPP-IV [Wronkowitz N, Görgens S W, Romacho T et al (2014) *Soluble DPP4 induces inflammation and proliferation of human smooth muscle cells via protease-activated receptor 2. Biochim Biophys Acta* 1842(9):1613-21]. After stimulation, F2rl1 promotes angiogenesis and inflammation and, therefore, could be an important target when treating DR. In addition, it has been reported that IL-1RA, a competitive antagonist of IL-1β receptors, is a substrate of DPP-4 [Zhang H, Maqsudi S, Rainczuk A et al (2015) *Identification of novel dipeptidyl peptidase 9 substrates by two-dimensional differential in-gel electrophoresis. FEBS J* 282(19):3737-57]. Therefore, the inhibition of DPP-4 could mitigate the deletereous role of IL-1β in the pathogenesis of DR by preventing the cleavage of IL-1RA.

Considering that surprisingly DPP-4 inhibitors could effectively reach the retina when administered topically to the surface of the eye (via cornea, sclera or conjunctiva), they suppose a real alternative also to the use of GLP-1 or of any GLP-1 agonist topically to the eye surface to reach the retina, since due to its non-peptide nature, they are more stable and easy to be manipulated when compositions comprising them are prepared.

The statistical analysis of the retrieved data was made. Normal distribution of the variables was evaluated using the Kolmogorov-Smirnov test. The data were presented as mean±SD. Comparisons of continuous variables were performed using the unpaired Student t-test. When multiple comparisons were performed, one-way ANOVA followed by the Bonferroni test was used. Comparisons between categorical variables were performed by Fisher's exact test. Levels of statistical significance were set at $p<0.05$.

All these data taken together provide first evidence that topical ocular administration (eye drops) of DPP-4 inhibitors has a potent effect in preventing the retinal neurodegenerative process that occurs in the early stages of diabetic retinopathy. The data also provide evidence that other retinal diseases in which neurodegeneration plays an essential role (related or not with GLP-1 receptor pathway) may be treated and/or prevented with the topical ocular administration (eye drops) of these compounds.

REFERENCES CITED IN THE APPLICATION

Schmidt et al., "Neurodegenerative Diseases of the Retina and Potential for the Protection and Recovery", *Current Neuropharmacology*—2008, Vol. No. 6, pp.: 164-178.

Simo et al., "Neurodegeneration is an early event in diabetic retinopathy: therapeutic implications", *Br. J. Ophthalmol.*—2012, vol. 96, pp. 1285-1290.

Urtti A et al., "Challenges and obstacles of ocular pharmacokinetics and drug delivery". *Adv. Drug. Deliv. Rev.* 2006, vol. 58, pp. 1131-1135.

Aiello et al., "Targeting Intraocular Neovascularization and Edema—One Drop at a Time", *N. Eng. J Med*—2008, vol. 359, pp. 967-969.

Malhotra et al., "Permeation through cornea", *Indian Journal of Experimental Biology*—2001, vol. no. 39, pp.: 11-24.

De Meester I et al., "CD26, let it cut or cut it down", *Immunol Today*—1999, vol. no. 20, pp.: 367-375.

Abbott, et al., "Cloning, expression and chromosomal localization of a novel human dipeptidyl peptidase (DPP) IV homolog, DPP8", *Eur J Biochem*—2000; vol. no. 267, pp.: 6140-50.

Kim et al., "The Nonglycemic Actions of Dipeptidyl Peptidase-4 Inhibitors"—*BioMed Research International* Volume 2014, Article ID 368703.

Baetta et al., "Pharmacology of dipeptidylpeptidase-4 inhibitors: similarities and differences", *Drugs*—2011, vol. no. 71, pp.: 1441-1467.

Prausnittz et al., "Permeability of Cornea, Sclera, and Conjunctiva: A Literature Analysis for Drug Delivery to the Eye", *Journal of Pharmaceutical Sciences*—1998, vol. no. 87(12), pp.: 1479-1488.

Jung et al., "Gemigliptin, a dipeptidyl peptidase-4 inhibitor, inhibits retinal pericyte injury in db/db mice and retinal neovascularization in mice", *Biochimica et Biophysica Acta, Molecular Basis of Disease*—2015, vol. no. 1852 (12), pp.: 2618-2629.

Anderson et al. "Glial and endothelial blood-retinal barrier responses to amyloid-beta in the neural retina of the rat". *Clin Ophthalmol*—2008, Vol. No.: 2, pp.: 801-816.

Simó R, Hernández C, "Novel approaches for treating diabetic retinopathy based on recent pathogenic evidence", *Prog Retin Eye Res*—2015, vol. no. 48, pp.: 160-80.

Simó R, Hernández C; European Consortium for the Early Treatment of Diabetic Retinopathy (EUROCONDOR). "Neurodegeneration in the diabetic eye: new insights and therapeutic perspectives", *Trends Endocrinol Metab*—, 2014; vol. no. 25(1), pp.: 23-33.

Bogdanov et al., "The db/db mouse: a useful model for the study of diabetic retinal neurodegeneration", *PLoS One*—2014, vol. no. 9(5):e97302.

Marmor et al., "Standard for clinical electroretinography", International Society for Clinical Electrophysiology of Vision (2004), *Doc Ophthalmol*—2004; vol. 108, pp.: 107-114.

Dietrich N, Kolibabka M, Busch S, et al (2016) *The DPP4 Inhibitor Linagliptin Protects from Experimental Diabetic Retinopathy.* PLoS One 11:e0167853

Wronkowitz N, Görgens S W, Romacho T et al (2014) *Soluble DPP4 induces inflammation and proliferation of human smooth muscle cells via protease-activated receptor 2.* Biochim Biophys Acta 1842(9):1613-21]

Zhang H, Maqsudi S, Rainczuk A et al (2015) *Identification of novel dipeptidyl peptidase 9 substrates by two-dimensional differential in-gel electrophoresis.* FEBS J 282(19): 3737-57

SEQUENCE LISTING

```
<160> NUMBER OF SEQ ID NOS: 3

<210> SEQ ID NO 1
<211> LENGTH: 31
<212> TYPE: PRT
<213> ORGANISM: Artificial
<220> FEATURE:
<223> OTHER INFORMATION: Liraglutide; analogue of glucagon like peptide-
      1 (7-37) (GLP-1(7-37))
<220> FEATURE:
<221> NAME/KEY: LIPID
<222> LOCATION: (20)..(20)
<223> OTHER INFORMATION: Lysine residue (K, Lys) comprises the
      lipophilic substituent N epsilon-(gamma-glutamyl(N-alfa-
      hexadecanoyl)) attached by an amide link to the amino group of the
      lysine side chain

<400> SEQUENCE: 1
```

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 2
<211> LENGTH: 44
<212> TYPE: PRT
<213> ORGANISM: Artificial
<220> FEATURE:
<223> OTHER INFORMATION: Lixisenatide; glucagon-like peptide-1 agonist;
      derived from exenatide
<220> FEATURE:
<221> NAME/KEY: MOD_RES
<222> LOCATION: (44)..(44)
<223> OTHER INFORMATION: X is a lysine residue in which the -COOH
      terminal has been modified by a -NH2 group

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Xaa
        35                  40

<210> SEQ ID NO 3
<211> LENGTH: 39
<212> TYPE: PRT
<213> ORGANISM: Artificial
<220> FEATURE:
<223> OTHER INFORMATION: Exenatide; glucagon-like peptide-1 agonist;
      synthetic version of hormone exendine-4 found in the saliva of the
      Gila monster
<220> FEATURE:
<221> NAME/KEY: MOD_RES
<222> LOCATION: (39)..(39)
<223> OTHER INFORMATION: X is a serine residue in which the -COOH
      terminal has been modified by a -NH2 group

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Xaa
        35
```

The invention claimed is:

1. A method for the topical eye treatment and/or prevention of diabetic retinopathy or microvascular impairment associated with diabetic retinopathy, comprising administering a dipeptidyl peptidase-4 inhibitor selected from the group consisting of sitagliptin, saxagliptin, vildagliptin, linagliptin, anagliptin, teneligliptin, alogliptin, trelagliptin, gemigliptin, omarigliptin, pharmaceutically acceptable salts thereof, and mixtures thereof, together with topical pharmaceutically or veterinary acceptable excipients and/or carriers, in a subject in need thereof, including a human.

2. The method according to claim 1, wherein the treatment and/or prevention of diabetic retinopathy or microvascular impairment associated with diabetic retinopathy is done by inhibition of retinal dipeptidyl peptidase-4.

3. The method according to claim 1, wherein treatment and/or prevention is for early stage diabetic retinopathy.

4. A method for the topical eye treatment and/or prevention of diabetic retinopathy, comprising administering a pharmaceutical or veterinary topical eye composition, which composition comprises an effective amount of a dipeptidyl peptidase-4 inhibitor selected from the group consisting of sitagliptin, saxagliptin, vildagliptin, linagliptin, anagliptin, teneligliptin, alogliptin, trelagliptin, gemigliptin, omarigliptin, and mixtures thereof, or a pharmaceutically or veterinary acceptable salt thereof, and mixtures thereof, together with topical pharmaceutically or veterinary acceptable excipients and/or carriers.

5. The method according to claim 4, wherein the pharmaceutical or veterinary topical eye composition further comprising an effective amount of a compound selected from the group consisting of mammal glucagon like peptide-1, liraglutide, exenatide, lixisenatide, or a pharmaceutically or veterinary acceptable salt thereof, and mixtures thereof.

6. The method according to claim 5, wherein the mammal glucagon like peptide-1 is the human glucagon-like peptide-1 (7-37) (UniProt: P01275), or a pharmaceutically or veterinary acceptable salt thereof.

7. The method according to claim 4, wherein the pharmaceutical or veterinary topical eye composition is selected from the group consisting of solutions, creams, lotions, unguents, emulsions, and suspensions.

8. The method according to claim 4, wherein the pharmaceutical or veterinary topical eye composition is an eye drop solution.

9. The method according to claim 4, wherein the pharmaceutical or veterinary topical eye composition is a sustained-release composition.

10. The method according to claim 4, wherein treatment and/or prevention is for early stage diabetic retinopathy.

11. The method according to claim 2, wherein the dipeptidyl peptidase-4 inhibitor is selected from the group consisting of sitagliptin, saxagliptin, vildagliptin, linagliptin, anagliptin, teneligliptin, alogliptin, trelagliptin, gemigliptin, omarigliptin, and mixtures thereof; or pharmaceutically acceptable salt(s) thereof.

12. The method according to claim 2, wherein treatment and/or prevention is for early stage diabetic retinopathy.

* * * * *